US009241970B2

(12) United States Patent
Tymianski

(10) Patent No.: US 9,241,970 B2
(45) Date of Patent: Jan. 26, 2016

(54) THERAPY FOR SUBARACHNOID HEMORRHAGE AND ISCHEMIA

(71) Applicant: NoNO Inc., Toronto (CA)

(72) Inventor: Michael Tymianski, Toronto (CA)

(73) Assignee: NoNO Inc. (CA)

( * ) Notice: Subject to any disclaimer, the term of this patent is extended or adjusted under 35 U.S.C. 154(b) by 0 days.

(21) Appl. No.: 13/774,053

(22) Filed: Feb. 22, 2013

(65) Prior Publication Data

US 2013/0156704 A1 Jun. 20, 2013

Related U.S. Application Data

(63) Continuation-in-part of application No. 13/713,489, filed on Dec. 13, 2012, now abandoned, and a continuation-in-part of application No. PCT/IB2012/057259, filed on Dec. 13, 2012.

(60) Provisional application No. 61/617,001, filed on Mar. 28, 2012, provisional application No. 61/570,264, filed on Dec. 13, 2011.

(30) Foreign Application Priority Data

Dec. 15, 2011 (CA) ..................................... 2762338

(51) Int. Cl.
| | |
|---|---|
| A61K 38/00 | (2006.01) |
| A61K 38/08 | (2006.01) |
| A61K 38/10 | (2006.01) |
| G01N 33/68 | (2006.01) |
| C07K 14/47 | (2006.01) |
| A61K 45/06 | (2006.01) |
| A61K 49/00 | (2006.01) |
| C07K 14/705 | (2006.01) |

(52) U.S. Cl.
CPC ............... *A61K 38/10* (2013.01); *A61K 38/08* (2013.01); *A61K 45/06* (2013.01); *A61K 49/00* (2013.01); *C07K 14/47* (2013.01); *C07K 14/70571* (2013.01); *G01N 33/6893* (2013.01); *A61K 38/00* (2013.01); *C07K 2319/10* (2013.01); *G01N 2800/2871* (2013.01)

(58) Field of Classification Search
None
See application file for complete search history.

(56) References Cited

U.S. PATENT DOCUMENTS

| | | | |
|---|---|---|---|
| 2005/0059597 A1* | 3/2005 | Tymianski | ...................... 514/12 |
| 2012/0208764 A1 | 8/2012 | Tymianski | |
| 2012/0269733 A1 | 10/2012 | Tymianski et al. | |
| 2014/0248257 A1 | 9/2014 | Tymianski et al. | |

FOREIGN PATENT DOCUMENTS

| | | |
|---|---|---|
| CA | 2524573 A1 | 11/2004 |
| WO | WO 2008/008348 A2 | 1/2008 |
| WO | WO 2008/014917 A1 | 2/2008 |
| WO | WO 2008/109010 A1 | 9/2008 |
| WO | WO 2010/144721 A2 | 12/2010 |
| WO | WO 2012/176172 A2 | 12/2012 |
| WO | WO 2013/088382 A1 | 6/2013 |

OTHER PUBLICATIONS

Ardizzone et al. 2007 "Src kinase inhibition improves acute outcomes after experimental intracerebral hemorrhage" Stroke 38:1621-1625.*
Kusaka et al. 2004 "Signaling pathways for early brain injury after subarachnoid hemorrhage" J Cerebral Blood flow and metabolism 24:916-925.*
Nelson et al. 2007 "Myristoyl-based transport of peptides into living cells" Biochem 46(51):14771-14781.*
Sam 2010 "Differential protein interactions of nmda receptor NR2 subunits" Doctoral thesis; University of Toronto. Published Jan. 11, 2011.*
Sturgill et al. 2009 "distinct domains within psd-95 mediate synaptic incorporation, stabilization, and activity-dependent trafficking" J neurosci 29(41):12845-12854.*
The Free Online Medical Dictionary 2001 "Subarachnoid Hemorrhage" accessed Aug. 6, 2013 from medical-dictionary.thefreedictionary.com/subarachnoid+hemorrhage.*
Cognosci 2007 "Novel therapeutic compounds for subarachnoid hemorrhage" www.cognosci.com/documents/sah_white_paper.pdf.*
Germano et al. 2007 "NMDA receptor antagonist felbamate reduces behavioral deficits and blood-brain barrier permeability changes after experimental subarachnoid hemorrhage in the rat" J neurotrauma 24(4):732-744.*
"Abstracts of the 46th Annual Congress of the Canadian Neurological Sciences Federation," Can J Neurol Sci, 38(3):1-94, (2011).
"Species Dosage Conversion Factors," National Cancer Institute (NCI), Frederick National Laboratory for Cancer Research, Laboratory Animal Sciences Program (LASP), Animal Care and Use Committee (ACUC) Guidelines, ACUC 42.00, 1 page, (2007). [Retrieved from the Internet Jul. 15, 2014: <URL: https://ncifrederick.cancer.gov/Lasp/Acuc/Frederick/Media/Documents/ACUC42.pdf>].

(Continued)

*Primary Examiner* — Gregory S Emch
*Assistant Examiner* — Adam M Weidner
(74) *Attorney, Agent, or Firm* — Alston & Bird LLP

(57) ABSTRACT

The application provides data from a clinical trial of a PSD-95 inhibitor in subjects undergoing endovascular repair of an aneurysm in or otherwise affecting the CNS. The subjects were stratified by whether the aneurysm ruptured before performing the endovascular surgery. Rupture is associated with higher mortality or increased debilitation if a subject survives. The trial provided evidence of significant benefit in subjects with and without aneurysm rupture before endovascular was surgery performed. Surprisingly, the subjects benefiting most from treatment as judged both by pathology and neurocognitive outcome were those in which the aneurysm had ruptured causing a subarachnoid hemorrhage. These data constitute evidence that a PSD-95 inhibitor is beneficial not only in ischemic and hemorrhagic stroke but in forms of hemorrhage in or affecting the CNS, particularly, subarachnoid hemorrhage.

23 Claims, 3 Drawing Sheets

(56) References Cited

OTHER PUBLICATIONS

Aarts et al., "Treatment of Ischemic Brain Damage by Perturbing NMDA Receptor-PSD-95 Protein Interactions," Science, 298(5594):846-850, (2002).
Bang et al., "Specific DWI lesion patterns predict prognosis after acute ischaemic stroke within the MCA territory," J Neurol Neurosurg Psychiatry, 76:1222-1228, (2005).
Bratane et al., "Neuroprotection by freezing ischemic penumbra evolution without cerebral blood flow augmentation with a postsynaptic density-95 protein inhibitor," Stroke, 42(11):3265-3270, (2011).
Brooks et al., "Frequency of thromboembolic events associated with endovascular aneurysm treatment: retrospective case series", Journal of Neurosurg, 108:1095-1100, (2008).
Cook et al., "Treatment of stroke with a PSD-95 inhibitor in the gyrencephalic primate brain," Nature, 483(7388):213-217, (2002).
Cronqvist et al., "Diffusion and perfusion MRI in patients with ruptured and unruptured intracranial aneurysms treated by endovascular coiling: complications, procedural results, MR findings and clinical outcome," Neuroradiology, 47:855-873, (2005).
Cui et al. "PDZ protein interactions underlying NMDA receptor-mediated excitotoxicity and neuroprotection by PSD-95 inhibitors," J. Neurosci., 27(37):9901-9915, (2007).
Davis et al., "Termination of Acute Stroke Studies Involving Selfotel Treatment," The Lancet, 349:32-32, (1997).
Donnan et al., "How to make better use of thrombolytic therapy in acute ischemic stroke," Nat Rev Neurol., 7(7): 400-409, (2011).
EPO Application No. 10786859.8, Supplementary European Search Report and European Search Opinion mailed Apr. 30, 2014.
EPO Application No. EP 12802409.8, Supplementary European Search Report and European Search Opinion mailed Nov. 12, 2014.
Fan et al., "N-Methyl-D-aspartate receptor subunit- and neuronal-type dependence of excitotoxic signaling through post-synaptic density 95," Journal of Neurochemistry, 115(4):1045-1056, (2010).
Fan, et al. "Interaction of postsynaptic density protein-95 with NMDA receptors influences excitotoxicity in the yeast artificial chromosome mouse model of Huntington's disease," J. Neurosci., 29(35):10928-10938, (2009).
Florio, et al., "Disruption of nNOS-PSD95 Protein-protein Interaction Inhibits Acute Thermal Hyperalgesia and Chronic Mechanical Allodynia in Rodents", Brit. J. Pharmacol., 158(2):494-506, (2009).
Haley et al., "A randomized, double-blind, vehicle-controlled trial of tirilazad mesylate in patients with aneurysmal subarachnoid hemorrhage: a cooperative study in North America," J Neurosurg, 86(3):467-474, (1997). Abstract Only.
Herce, et al., "Molecular dynamics simulations suggest a mechanism for translocation of the HIV-1 TAT peptide across lipid membranes," Proc. Natl. Acad. Sci. U. S. A., 104(52)20805-20810, (2007).
Hill et al., "Safety and efficacy of NA-1 in patients with iatrogenic stroke after endovascular aneurysm repair (ENACT): a phase 2, randomised, double-blind, placebo-controlled trial," The Lancet Neurology, 11(11):942-950, (2012).
Horn et al., "Very Early Nimodipine Use in Stroke (VENUS): A Randomized, Double-Blind, Placebo-Controlled Trial," Stroke, 32:461-465, (2001).
Kaufmann et al., "Complications of Diagnostic Cerebral Angiography: Evaluation of 19 826 Consecutive Patients", Radiology, 243(3):812-819, (2007).
Kleckner et al., "Subtype-Selective Antagonism of N-Methyl-o-Aspartate Receptors by Felbamate: Insights into the Mechanism of Action," JPET, 289(2):898-894, (1999).
Lanzino et al., "Double-blind, randomized, vehicle-controlled study of high-dose tirilazad mesylate in women with aneurysmal subarachnoid hemorrhage. Part II. A cooperative study in North America," J Neurosurg, 90(6)1018-1024 , (1999). Abstract Only.
Lees, "Cerestat and other NMDA antagonists in ischemic stroke," Neurology, 49(Suppl 4):S66-S69, (1997).
Li, "Pharmacologically Induced Histamine Release: Sorting Out Hypersensitivity Reactions to Opioids," Publication, 35(4):1,14-16, (2006).
Martel, et al., "Inhibiting pro-death NMDA receptor signaling dependent on the NR2 PDZ ligand may not affect synaptic function or synaptic NMDA receptor signaling to gene expression," Channels (Austin), 3(1)12-15, (2009).
Miyazawa et al., "Effect of mild hypothermia on focal cerebral ischemia. Review of experimental studies," Neurol Res, 25(5):457-464, (2003), Abstract Only.
Morgan et al., "Chapter 9: Neuromuscular Blocking Agents," Clinical Anesthesiology, 4th Edition, McGraw-Hill Companies, Inc., 32 pages, (2006). [Retrieved from the Internet Jan. 7, 2014: <URL: http://bentollenaar.com/_MM_Book/Ch.9.htm>].
Sena et al., "Systematic Review and Meta-Analysis of the Efficacy of Tirilazad in Experimental Stroke," Publication,Stroke, 38:388-394, (2007). Retrieved from the Internet Dec. 3, 2014: <URL: http://stroke.ahajournals.org/content/38/2/388/>].
Soriano, et al., "Specific targeting of pro-death NMDA receptor signals with differing reliance on the NR2B PDZ ligand," J. Neurosci., 28(42):10696-1071015, (2008).
Sun, et al. "Effectiveness of PSD95 inhibitors in permanent and transient focal ischemia in the rat," Stroke, 39(9):2544-2553, (2008).
Todd et al., "Mild Intraoperative Hypothermia during Surgery for Intracranial Aneurysm," N Engl J Med, 352:135-145, (2005).
U.S. Appl. No. 13/377,523, Final Office Action mailed Jan. 15, 2014.
U.S. Appl. No. 13/377,523, Non-Final Office Action mailed Apr. 29, 2013.
U.S. Appl. No. 13/377,523, Notice of Allowance and Examiner Initiated Interview Summary mailed Sep. 12, 2014.
Westermaier, "Neuroprotective Treatment Strategies for Delayed Cerebral Ischemia after Subarachnoid Hemorrhage—Review of Literature and Future Prospects," J Neural Neurophysiol, 5(1):1-8, (2013).
WIPO Application No. PCT/IB2012/053178, PCT International Preliminary Report on Patentability mailed Jan. 9, 2014.
WIPO Application No. PCT/IB2012/053178, PCT International Search Report and Written Opinion of the International Searching Authority mailed Oct. 10, 2012.
WIPO Application No. PCT/IB2012/057259, PCT International Preliminary Report on Patentability mailed Jun. 26, 2014.
WIPO Application No. PCT/IB2012/057259, PCT International Search Report and Written Opinion of the International Searching Authority mailed Apr. 12, 2013.
WIPO Application No. PCT/US2010/038200, International Search Report and Written Opinion of the International Searching Authority, mailed Jun. 10, 2010.
WIPO Application No. PCT/US2010/038200, PCT International Preliminary Report on Patentability mailed Dec. 22, 2011.
Zaleska et al., "The development of stoke therapeutics: Promising mechanisms and translational challenges," Neuropharmacology, 56:329-341, (2009).
ClinicalTrials.gov Identifier NCT00728182, "Evaluating Neuroprotection in Aneurysm Coiling Therapy (ENACT)," ClinicalTrials.gov, Full Text View, U.S. National Institutes of Health, Aug. 1, 2008. [Retrieved from the Internet Feb. 18, 2015: <URL: https://clinicaltrials.gov/ct2/show/study/NCT00728182>].
EPO Application No. 12857611.3, Supplementary European Search Report and European Search Opinion mailed Aug. 21, 2015.
Grasso et al., "An overview of new pharmacological treatments for cerebrovascular dysfunction after experimental subarachnoid hemorrhage," Brain Research Reviews, 44(1):49-63, (2004).

\* cited by examiner

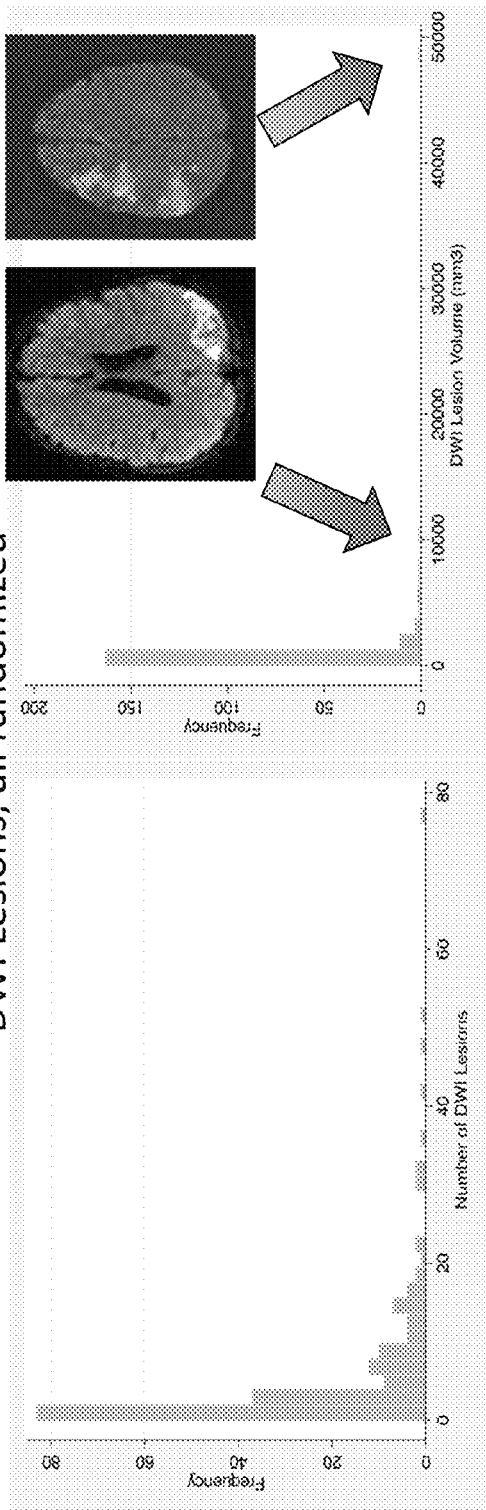
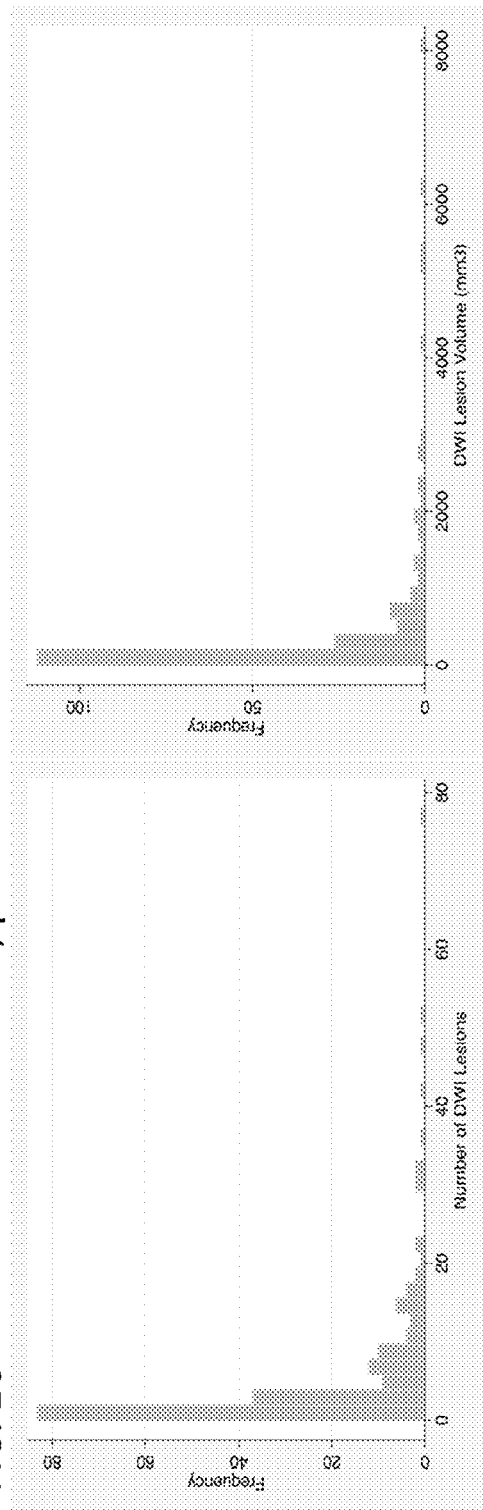
FIG. 1B
FIG. 1C

* Full set of MRIs (pre- and post-coiling available for 2 of the 3, and included in MRI analysis. 1 patient died before day 2-4 MRI could be performed.
** Full set of MRIs (pre- and post-coiling available for all 3, and included in MRI analysis.

```
                           SEQUENCE LISTING

<160> NUMBER OF SEQ ID NOS: 69

<210> SEQ ID NO 1
<211> LENGTH: 10
<212> TYPE: PRT
<213> ORGANISM: Human immunodeficiency virus

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Human immunodeficiency virus

<400> SEQUENCE: 3

Phe Gly Arg Lys Lys Arg Arg Gln Arg Arg Arg
1               5                   10

<210> SEQ ID NO 4
<211> LENGTH: 12
<212> TYPE: PRT
<213> ORGANISM: Human immunodeficiency virus

<400> SEQUENCE: 4

Gly Arg Lys Lys Arg Arg Gln Arg Arg Arg Pro Gln
1               5                   10

<210> SEQ ID NO 5
<211> LENGTH: 9
<212> TYPE: PRT
<213> ORGANISM: Homo sapiens

<400> SEQUENCE: 5

Lys Leu Ser Ser Ile Glu Ser Asp Val
1               5

<210> SEQ ID NO 6
<211> LENGTH: 20
<212> TYPE: PRT
<213> ORGANISM: Human immunodeficiency virus

<400> SEQUENCE: 6

Tyr Gly Arg Lys Lys Arg Arg Gln Arg Arg Arg Lys Leu Ser Ser Ile
1               5                   10                  15

Glu Ser Asp Val
            20

<210> SEQ ID NO 7
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Gln, Ala or an analogue thereof
<220> FEATURE:
<221> NAME/KEY: MOD_RES
<222> LOCATION: (2)..(2)
<223> OTHER INFORMATION: Thr or Ser
<220> FEATURE:
<221> NAME/KEY: MOD_RES
<222> LOCATION: (3)..(3)
<223> OTHER INFORMATION: Ala, Gln, Asp, Asn, (N-methyl)-Ala,
      (N-methyl)-Gln, (N-methyl)-Asp, (N-methyl)-Asn or an analogue
      thereof
<220> FEATURE:
<223> OTHER INFORMATION: See specification as filed for detailed
      description of substitutions and preferred embodiments

<400> SEQUENCE: 7

Xaa Xaa Xaa Val
1

<210> SEQ ID NO 8
<211> LENGTH: 22
<212> TYPE: PRT
<213> ORGANISM: Human immunodeficiency virus
<220> FEATURE:
<221> NAME/KEY: MOD_RES
<222> LOCATION: (1)..(22)
<223> OTHER INFORMATION: D-amino acid residues

<400> SEQUENCE: 8

Val Asp Ser Glu Ile Ser Ser Leu Lys Arg Arg Arg Gln Arg Arg Lys
1               5                   10                  15

Lys Arg Gly Tyr Ile Asn
            20

<210> SEQ ID NO 9
<211> LENGTH: 20
<212> TYPE: PRT
<213> ORGANISM: Human immunodeficiency virus

<400> SEQUENCE: 9

Arg Arg Arg Gln Arg Arg Lys Lys Arg Gly Tyr Lys Leu Ser Ser Ile
1               5                   10                  15

Glu Ser Asp Val
            20

<210> SEQ ID NO 10
<211> LENGTH: 5
<212> TYPE: PRT
<213> ORGANISM: Homo sapiens

<400> SEQUENCE: 10

Ile Glu Ser Asp Val
1               5

<210> SEQ ID NO 11
<211> LENGTH: 20
<212> TYPE: PRT
<213> ORGANISM: Homo sapiens

<400> SEQUENCE: 11
```

```
Phe Asn Gly Ser Ser Asn Gly His Val Tyr Glu Lys Leu Ser Ser Ile
1               5                   10                  15

Glu Ser Asp Val
            20

<210> SEQ ID NO 12
<211> LENGTH: 4
<212> TYPE: PRT
<213> ORGANISM: Homo sapiens

<400> SEQUENCE: 12

Glu Ser Asp Val
1

<210> SEQ ID NO 13
<211> LENGTH: 20
<212> TYPE: PRT
<213> ORGANISM: Homo sapiens

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 20
<212> TYPE: PRT
<213> ORGANISM: Homo sapiens

<400> SEQUENCE: 14

Arg Arg Ala Ile Glu Arg Glu Glu Gly Gln Leu Gln Leu Cys Ser Arg
1               5                   10                  15

His Arg Glu Ser
            20

<210> SEQ ID NO 15
<211> LENGTH: 20
<212> TYPE: PRT
<213> ORGANISM: Homo sapiens

<400> SEQUENCE: 15

Thr Gln Gly Phe Pro Gly Pro Cys Thr Trp Arg Arg Ile Ser Ser Leu
1               5                   10                  15

Glu Ser Glu Val
            20

<210> SEQ ID NO 16
<211> LENGTH: 20
<212> TYPE: PRT
<213> ORGANISM: Homo sapiens

<400> SEQUENCE: 16

Ala Val Ser Arg Lys Thr Glu Leu Glu Glu Tyr Gln Arg Thr Ser Arg
1               5                   10                  15

Thr Cys Glu Ser
            20

<210> SEQ ID NO 17
<211> LENGTH: 20
<212> TYPE: PRT
<213> ORGANISM: Homo sapiens
```

```
<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Homo sapiens

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Homo sapiens

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Homo sapiens

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Homo sapiens

<400> SEQUENCE: 21

Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Homo sapiens

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20
```

-continued

```
<210> SEQ ID NO 23
<211> LENGTH: 20
<212> TYPE: PRT
<213> ORGANISM: Homo sapiens

<400> SEQUENCE: 23

His Thr Gly Thr Ala Ile Arg Gln Ser Ser Gly Leu Ala Val Ile Ala
1               5                   10                  15

Ser Asp Leu Pro
            20

<210> SEQ ID NO 24
<211> LENGTH: 20
<212> TYPE: PRT
<213> ORGANISM: Homo sapiens

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Homo sapiens

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 11
<212> TYPE: PRT
<213> ORGANISM: Human immunodeficiency virus

<400> SEQUENCE: 26

Gly Arg Lys Lys Arg Arg Gln Arg Arg Pro
1               5                   10

<210> SEQ ID NO 27
<211> LENGTH: 4
<212> TYPE: PRT
<213> ORGANISM: Homo sapiens

<400> SEQUENCE: 27

Ser Thr Val Val
1

<210> SEQ ID NO 28
<211> LENGTH: 4
<212> TYPE: PRT
<213> ORGANISM: Homo sapiens

<400> SEQUENCE: 28

His Arg Glu Ser
1

<210> SEQ ID NO 29
<211> LENGTH: 4
<212> TYPE: PRT
<213> ORGANISM: Homo sapiens
```

<400> SEQUENCE: 29

Glu Ser Glu Val
1

<210> SEQ ID NO 30
<211> LENGTH: 4
<212> TYPE: PRT
<213> ORGANISM: Homo sapiens

<400> SEQUENCE: 30

Thr Cys Glu Ser
1

<210> SEQ ID NO 31
<211> LENGTH: 4
<212> TYPE: PRT
<213> ORGANISM: Homo sapiens

<400> SEQUENCE: 31

Gly Thr Ser Ile
1

<210> SEQ ID NO 32
<211> LENGTH: 4
<212> TYPE: PRT
<213> ORGANISM: Homo sapiens

<400> SEQUENCE: 32

Ala Thr Gly Leu
1

<210> SEQ ID NO 33
<211> LENGTH: 4
<212> TYPE: PRT
<213> ORGANISM: Homo sapiens

<400> SEQUENCE: 33

Ser Val Lys Ile
1

<210> SEQ ID NO 34
<211> LENGTH: 4
<212> TYPE: PRT
<213> ORGANISM: Homo sapiens

<400> SEQUENCE: 34

Ser Asp Leu Pro
1

<210> SEQ ID NO 35
<211> LENGTH: 4
<212> TYPE: PRT
<213> ORGANISM: Homo sapiens

<400> SEQUENCE: 35

Glu Thr Val Ala
1

<210> SEQ ID NO 36
<211> LENGTH: 4
<212> TYPE: PRT
<213> ORGANISM: Homo sapiens

<400> SEQUENCE: 36

```
Glu Thr Met Ala
1

<210> SEQ ID NO 37
<211> LENGTH: 20
<212> TYPE: PRT
<213> ORGANISM: Human immunodeficiency virus

<400> SEQUENCE: 37

Tyr Gly Arg Lys Lys Arg Arg Gln Arg Arg Arg Lys Leu Ser Ser Ile
1               5                   10                  15

Glu Thr Asp Val
            20

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Asp, Asn or Gln
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Asp, Glu, Gln or Asn
<220> FEATURE:
<221> NAME/KEY: MOD_RES
<222> LOCATION: (4)..(4)
<223> OTHER INFORMATION: Val or Leu

<400> SEQUENCE: 38

Xaa Xaa Xaa Xaa
1

<210> SEQ ID NO 39
<211> LENGTH: 4
<212> TYPE: PRT
<213> ORGANISM: Homo sapiens

<400> SEQUENCE: 39

Glu Thr Asp Val
1

<210> SEQ ID NO 40
<211> LENGTH: 4
<212> TYPE: PRT
<213> ORGANISM: Homo sapiens

<400> SEQUENCE: 40

Glu Thr Glu Val
1

<210> SEQ ID NO 41
<211> LENGTH: 4
<212> TYPE: PRT
<213> ORGANISM: Homo sapiens

<400> SEQUENCE: 41

Asp Thr Asp Val
```

```
<210> SEQ ID NO 42
<211> LENGTH: 4
<212> TYPE: PRT
<213> ORGANISM: Homo sapiens

<400> SEQUENCE: 42

Asp Thr Glu Val
1

<210> SEQ ID NO 43
<211> LENGTH: 9
<212> TYPE: PRT
<213> ORGANISM: Homo sapiens

<400> SEQUENCE: 43

Lys Leu Ser Ser Ile Glu Thr Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Glu Lys Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Arg Gln Arg Asp Gly Glu Arg Pro
1               5
```

<210> SEQ ID NO 48
<211> LENGTH: 13
<212> TYPE: PRT
<213> ORGANISM: Human immunodeficiency virus

<400> SEQUENCE: 48

Tyr Gly Arg Lys Lys Arg Arg Gln Arg Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid other than Tyr or not present

<400> SEQUENCE: 49

Xaa Gly Arg Lys Lys Arg Arg Gln Arg Arg Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 50

Xaa Gly Lys Lys Lys Lys Lys Gln Lys Lys Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 51

Xaa Arg Lys Lys Arg Arg Gln Arg Arg Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

```
<400> SEQUENCE: 52

Xaa Gly Ala Lys Lys Arg Arg Gln Arg Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 53

Xaa Ala Lys Lys Arg Arg Gln Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 54

Xaa Gly Arg Lys Ala Arg Arg Gln Arg Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 55

Xaa Arg Lys Ala Arg Arg Gln Arg Arg
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 56

Xaa Gly Arg Lys Lys Ala Arg Gln Arg Arg
1               5                   10

<210> SEQ ID NO 57
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 57

Xaa Arg Lys Lys Ala Arg Gln Arg Arg Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 58

Xaa Gly Arg Lys Lys Arg Arg Gln Ala Arg Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 59

Xaa Arg Lys Lys Arg Arg Gln Ala Arg Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 60

Xaa Gly Arg Lys Lys Arg Arg Gln Arg Ala Arg
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Any amino acid or not present

<400> SEQUENCE: 61

Xaa Arg Lys Lys Arg Arg Gln Arg Ala Arg
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 62

Xaa Arg Arg Pro Arg Arg Pro Arg Arg Pro Arg Arg
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 63

Xaa Arg Arg Ala Arg Arg Ala Arg Arg Ala Arg Arg
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 64

Xaa Arg Arg Arg Ala Arg Arg Arg Ala Arg Arg
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 65

Xaa Arg Arg Arg Pro Arg Arg Arg Pro Arg Arg
```

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 66

Xaa Arg Arg Pro Arg Arg Pro Arg Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 67

Xaa Arg Arg Ala Arg Arg Ala Arg Arg
1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Leu Gly Phe
1

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or not present

<400> SEQUENCE: 69

Xaa Phe Gly Arg Lys Lys Arg Arg Gln Arg Arg Arg
1               5                   10

THERAPY FOR SUBARACHNOID HEMORRHAGE AND ISCHEMIA

CROSS-REFERENCE TO RELATED APPLICATIONS

The present application is a continuation-in-part of U.S. application Ser. No. 13/713,489, filed Dec. 13, 2012 and PCT/IB2012/057259 filed Dec. 13, 2012, both of which claim the benefit of U.S. 61/617,001 filed Mar. 28, 2012, U.S. 61/570,264, filed Dec. 13, 2011 and CA 2762338, filed Dec. 15, 2011, each incorporated by reference in its entirety for all purposes.

SEQUENCE LISTING

The application contains a Sequence Listing which has been submitted in ASCII format via EFS-Web and is hereby incorporated by reference in its entirety. The ASCII copy, created on Feb. 21, 2013, is named 428787SEQLIST.txt and is 16 kilobytes in size.

BACKGROUND

Each year approximately 800,000 individuals in the USA suffer a stroke, with yearly direct and indirect societal costs that exceed $40 B. Stroke ranks third among all causes of death. Currently, only therapies that induce reperfusion of an ischemic brain are widely approved as treatments for acute stroke (e.g., thrombolysis with alteplase (tissue plasminogen activator or rt-PA). These balance improved overall outcome with the potential for serious complications and are underused. Safe pharmacological neuroprotection, brain salvage by enhancing the brain's resilience to ischemia, could dramatically enhance the number of patients that could benefit from acute stroke treatment. However, over decades, research has failed to translate over 1000 neuroprotective treatments from discovery in cells and rodents to utility in humans, and clinical trials of putative neuroprotectants have failed. This scientific crisis gave rise to a prevailing paradigm that pharmacological neuroprotection is not feasible or practicable in humans. Thus there is an urgent unmet need to determine whether or not neuroprotection in humans is possible.

Stroke can be the result of ischemia or hemorrhage. Hemorrhagic stroke accounts for about 17% of strokes but gives rise to a disproportionate share of deaths and debilitating injury. Hemorrhagic stroke is aggravated rather than alleviated by the only approved stroke drugs, such as tPA, which act to restore blood flow. Too often, the time required to bring a subject to a hospital, reach an initial diagnosis and perform a brain scan to distinguish between ischemic and hemorrhagic stroke would place a subject outside the window in which tPA can be effective. Thus, many ischemic stroke subjects, who could benefit from tPA, do not receive it.

Hemorrhage in or proximate to the CNS can also occur independently of ischemic stroke, particularly in subarachnoid hemorrhages, and dural or subdural hematoma and brain contusions. Such hemorrhages can arise as a result of physical trauma, such as a fall or other blow to the head or from shaken baby syndrome. Although the immediate symptoms of such hemorrhages can range from deceptively mild to severe, they can all rapidly become severe and life threatening. Such hemorrhages are thus a life-threatening emergency that even with the best current treatment often results in death or debilitating injury.

Subarachnoid Hemorrhage (SAH) is characterized by bleeding into the subarachnoid space. SAH is a serious, acute, life-threatening event that can result in chronic debilitation. In about 85% of cases of spontaneous SAH, the cause is the rupture of an intracranial aneurysm, termed aneurysmal SAH. Aneurysmal SAH most commonly affects people between the ages of 40 and 60 years, and is more likely to occur in women. The incidence of aneurysmal SAH is 10 in every 100,000 individuals per year in the U.S. Other less common causes of SAH include conditions such as vascular malformations. Acquired risk factors include high blood pressure, alcohol abuse, drug abuse, smoking, and contraceptive use. Other risk factors include aneurysm in other blood vessels, fibromuscular dysplasia and other connective tissue disorders, and history of polycystic kidney disease.

SAH is a multiphasic event, with an acute brain insult that occurs at the time of the initial bleed which is followed by secondary potentially injurious events such as ischemia that occur from cerebral vasospasm and hydrocephalus. In the acute SAH-induced injury, distribution of blood in the subarachnoid space, elevation of intracranial pressure (ICP), reduced cerebral perfusion pressure (CPP) and cerebral blood flow (CBF) initiate an acute injury cascade that produces transient brain ischemia, brain trauma due to the impulse produced by the sudden rise in ICP and, in some cases, brain injury due to intracerebral hematoma formation. Additionally, these initial events may lead to direct microvascular injury, plugging of vessels and release of vasoactive substances by platelet aggregates.

Secondary ischemic processes include anaerobic cellular respiration, energy depletion, impaired protein synthesis, excitotoxicity, free radical attack, neuronal stress, deoxyribonucleic acid (DNA) damage, apoptosis and necrosis, alterations in nitric oxide (NO)/nitric oxide synthase (NOS) pathways and lipid peroxidation. Although there is broad agreement about the range of secondary processes that may participate in producing brain injury following SAH, the precise contribution of individual mechanisms during the acute injury period remain incompletely understood.

Cerebral ischemia in SAH is the result of cerebral arterial vasospasm, and complicates the clinical course of approximately 30% of cases. The incidence of clinically-relevant vasospasm in SAH is highest between days 5 and 12 after the SAH. However, this complication is quite uncommon in the first three days after a SAH. A patient's ultimate clinical outcome after a SAH likely depends on the several factors, including demographic factors such as age and co-morbidities, the severity of the SAH, and the various complications of the SAH such as hydrocephalus and vasospasm. Thus, cerebral ischemia due to vasospasm is not the sole contributor to an adverse clinical outcome from SAH as symptoms appear immediately after rupture.

A different form of treatment for stroke and related conditions is now in clinical trials (see WO 2010144721 and Aarts et at, Science 298, 846-850 (2002)). This treatment uses TAT-NR2B9C, also known as Tat-NR2B9c (YGRKKRRQR-RRKLSSIESDV; SEQ ID NO:6], an agent that inhibits PSD-95 binding to NMDAR 2 family members, thus reducing excitotoxicity induced by cerebral ischemia. Treatment has been reported to reduce infarction size and functional deficits in ischemic stroke and traumatic brain injuries.

SUMMARY OF THE CLAIMED INVENTION

The invention provides methods of treating a damaging effect of subarachnoid hemorrhage in a subject, comprising administering an agent that inhibits binding of PSD-95 to an NMDAR2 subunit to a subject having a subarachnoid hemorrhage. In some methods, the subarachnoid hemorrhage is the result of physical trauma. In some methods, the subarachnoid hemorrhage occurs spontaneously. In some methods, the subarachnoid hemorrhage is due to a ruptured aneurysm. In some methods, the subarachnoid hemorrhage is due to arteriovenous malformation. In some methods, the agent inhibits development of neurocognitive deficits in the subject. In some methods, the agent inhibits development of infarctions detectable by MRI. In some methods, the subject receives endovascular surgery to repair a leaking blood vessel causing the subarachnoid hemorrhage. In some methods, the agent reduces pain resulting from endovascular surgery. In some methods, the pain is along a path traversed by an endoscope used in performing the endoscopic surgery. In some methods, the agent is administered by day 4 post rupture causing the subarachnoid hemorrhage. In some methods, the agent is administered on multiple occasions within twelve days post rupture causing the subarachnoid hemorrhage. In some methods, the agent is administered twice daily for at least two days or once daily for at least three days. In some methods, the dose of the agent is 1-3 mg/kg.

The invention further provides methods of treating a damaging effect of intracerebral hemorrhage in a subject, comprising administering an agent that inhibits binding of PSD-95 to NMDAR2 subunit to a subject having an intracerebral hemorrhage. In some methods, the intracerebral hemorrhage is due to high blood pressure. In some methods, the intracerebral hemorrhage is due to a drug. In some methods, the drug is an anti-coagulant. In some methods, the agent inhibits development of neurocognitive deficits in the subject. In some methods, the agent inhibits development of infarcts in the CNS detectable by MRI. In some methods, the agent is administered before, during or after surgery to repair a blood vessel causing the hemorrhage. In some methods, the agent is administered before, during or after administering another agent effect to reduce damaging effects of intracerebral hemorrhage.

The invention further provides an agent that inhibits binding of PSD-95 to an NMDAR2 subunit for use in reducing a damaging effect of ischemia or hemorrhage in or otherwise affecting the CNS of a subject and reducing pain in the subject from surgery to remediate the ischemia or hemorrhage. In some methods, the surgery is endovascular surgery. In some methods, the pain is along a path traversed by an endoscope used in performing the endoscopic surgery.

The invention further provides a method of reducing pain, comprising administering an agent that inhibits binding of PSD-95 to an NMDAR2 subunit to a subject receiving endovascular surgery wherein the agent reduces pain in the subject resulting from the endovascular surgery. In some methods, the pain is along a path traversed by an endoscope used in performing the endoscopic surgery.

The invention further provides methods of inhibiting a damaging effect of ischemia or hemorrhage in or otherwise affecting the CNS in a subject comprising administering to a subject having or suspect of having ischemia or hemorrhage in or otherwise affecting the CNS an effective regime of an agent that inhibits binding of PSD95 to an NMDAR2 subunit, wherein the subject has not been given a scan to distinguish ischemia from hemorrhage when the administering is performed. In some methods, the subject has a hemorrhage in or otherwise affecting the CNS. In some methods, the subject is not subject to reperfusion therapy.

The invention further provides methods of treating a damaging effect of ischemia or hemorrhage on the central nervous system, comprising administering an agent that inhibits binding of PSD-95 to NMDAR2 subunits to a subject having or at risk of ischemia or hemorrhage. In some methods, the agent is administered in conjunction with reperfusion therapy. Some methods treat a damaging effect of hemorrhagic stroke. In some methods, the agent is administered before, during or after endovascular repair of the hemorrhage. In some methods, the agent is administered before, during or after treatment with other drugs for the treatment of hemorrhages affecting the central nervous system.

The invention further provides an agent that inhibits binding of PSD95 to an NMDAR2 subunit for use in treatment of an ischemic stroke that transforms to a hemorrhagic stroke as a result of reperfusion, wherein the agent inhibits damaging effects of the ischemic and hemorrhagic stroke.

The invention further provides methods of treating a subject population presenting sign(s) and/or symptom(s) of ischemia, comprising administering an agent, which agent inhibits binding of PSD-95 inhibitor to an NDMAR2 subunit or nNOS, to the subjects; wherein the subjects are analyzed for unacceptable risk of side effects of reperfusion therapy, and subjects without unacceptable risk of side effects receive reperfusion therapy and subjects with unacceptable risk of side effects do not receive reperfusion therapy, optionally wherein the agent is a peptide that inhibits binding of PSD95 to an NMDAR2 subunit or nNOS, and the peptide is linked to an internalization peptide or is lipidated to increase across a cell membrane or the blood brain barrier.

In any of the above methods or agent, the agent can be a peptide having an amino acid sequence consisting or comprising of $X_1tSX_2V$ (SEQ ID NO:7), wherein t and S are alternative amino acids, $X_1$ is selected from among E, Q, and A, or an analogue thereof, $X_2$ is selected from among A, Q, D, N, (N-Methyl)-A, (N-methyl)-Q, (N-methyl)-D, and (N-methyl)-N or an analog thereof, and the peptide is linked at its N-terminal amino acid to an internalization peptide. In any of the above methods and agents, the agent can have an amino acid sequence consisting or comprising of YGRKKRRQR-RRKLSSIESDV (SEQ ID NO:6) or YGRKKRRQR-RRKLSSIETDV (SEQ ID NO:37). In any of the above methods, the peptide or other agent can be linked to an internalization peptide or lipidated thereby facilitating passage of the peptide across a cell membrane or the blood brain barrier. Some peptides or other agents are myristoylated. Peptides are preferably myristoylated at the N-terminus.

The invention further provides methods of screening a compound for activity useful in treating or effecting prophylaxis of stroke or hemorrhage in or otherwise affecting the CNS, comprising administering the compound to humans undergoing an endovascular repair procedure affecting the central nervous system, and determining whether the compound reduces the number of infarcts observed by MRI compared with a negative control. In some methods, the MRI imaging includes DWI MRI. In some methods, the MRI imaging includes FLAIR MRI. In some methods, the MRI imaging includes DWI and FLAIR MRI and infarcts resulting from the endovascular procedure are determined by identifying infarcts present on both DWI and FLAIR MRI.

The invention further provides an isolated peptide having an amino acid sequence consisting or comprising of $X_1tSX_2V$ (SEQ ID NO:7), wherein t and S are alternative amino acids, $X_1$ is selected from among E, Q, and A, $X_2$ is selected from among A, Q, D, N, (N-Methyl)-A, (N-methyl)-Q, (N-methyl)-D, and (N-methyl)-N, wherein the peptide is lipidated at the N-terminal amino acid. Some peptides have an amino acid sequence comprising or consisting of KLSSIESDV or KLSSIETDV.

BRIEF DESCRIPTION OF THE FIGURES

FIG. 1B, C: Distribution of DWI MRI-detectable lesion numbers and lesion volumes for all randomized patients who underwent a day 2-4 MRI (B; n=184), and for patients whose strokes were <10 cc's (C; n=182). Due to the extremely skewed distribution of the data, means and their standard deviations are expected to be highly affected by outliers. Insets in B provide representative slices of DWI MRI scans from the two patients who experienced large strokes (>10 cc's) as a result of procedural complications. As the counts of lesions are independent of volume, counts are less sensitive to large strokes.

DEFINITIONS

Figure 1A:
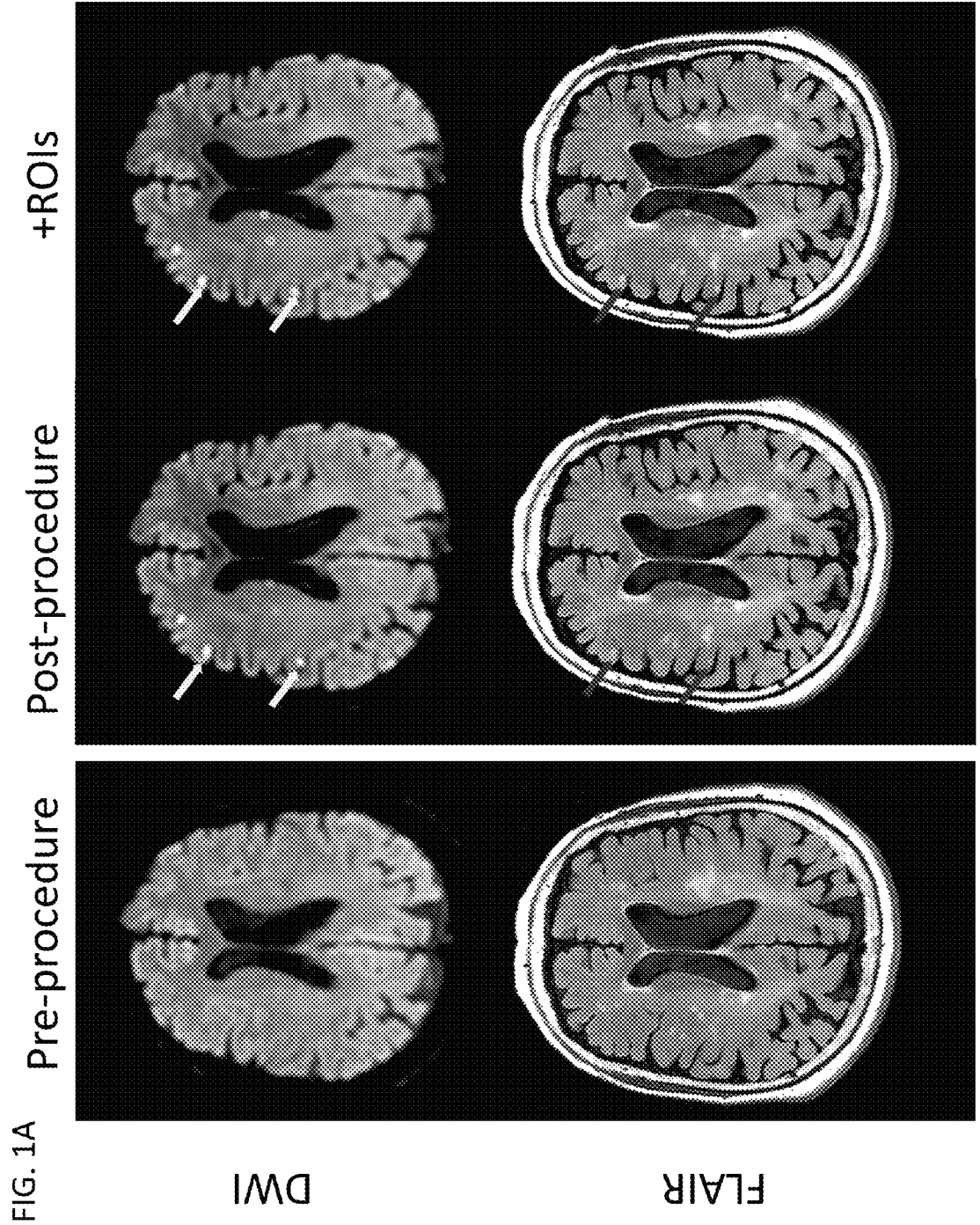
FIG. 1A. Sample DWI and FLAIR MRI scans of a single patient taken on enrollment (Pre-procedure) and on day 2 after the endovascular procedure (Post-procedure). Arrows indicate examples of DWI-positive embolic strokes (upper panels) and their FLAIR-positive counterparts (lower panels). Rightmost panels (ROIs) indicate selection of the regions of interest used to count the numbers and calculate the volumes of the ischemic lesions.

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

The term "PDZ domain" refers to a modular protein domain of about 90 amino acids, characterized by significant sequence identity (e.g., at least 60%) to the brain synaptic protein PSD-95, the *Drosophila* septate junction protein Discs-Large (DLG), and the epithelial tight junction protein ZO1 (ZO1). PDZ domains are also known as Discs-Large homology repeats ("DHRs") and GLGF (SEQ ID NO:68) repeats. PDZ domains generally appear to maintain a core consensus sequence (Doyle, D. A., 1996, Cell 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA including the various subunit forms described below. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), in which the composition consists essentially of a single macromolecular species. The term isolated or purified does not necessarily exclude the presence of other components intended to act in combination with an isolated species. For example, an internalization peptide can be described as isolated notwithstanding that it is linked to an active peptide or combined with a pharmaceutically acceptable excipient.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity.

Individual peptidomimetic residues can be joined by peptide bonds, other chemical bonds or coupling means, such as, e.g., glutaraldehyde, N-hydroxysuccinimide esters, bifunctional maleimides, $N_jN$-dicyclohexylcarbodiimide (DCC) or $N_5N$-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$.—), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, NY).

Mimetics of aromatic amino acids can be generated by replacing by, e.g., D- or L-naphylalanine; D- or L-phenylglycine; D- or L-2 thieneylalanine; D- or L-1, -2,3-, or A-pyreneylalanine; D- or L-3 thieneylalanine; D- or L-(2- pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R—N═C═N—R═) such as, e.g., 1-cyclohexyl-3(2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

The peptidomimetics of the invention can also include a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110:1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114:10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777 '. Secondary structures of polypeptides can be analyzed by, e.g., high-field .sup. $^1$H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

Peptidomimetics can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors, e.g., NMDAR2B.

The term "subject" includes humans and veterinary animals, such as mammals, as well as laboratory animal models, such as mice or rats used in preclinical studies.

The term "agent" includes any compound including compounds with or without pharmaceutical activity, natural compounds, synthetic compounds, small molecules, peptides and peptidomimetics.

The term "pharmacologic agent" means an agent having a pharmacological activity. Pharmacological agents include compounds that are known drugs, compounds for which pharmacological activity has been identified but which are undergoing further therapeutic evaluation in animal models or clinical trials. A chimeric agent comprises a pharmacologic agent linked to an internalization peptide. An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A tat peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. Such can be accomplished by not substituting or deleting the R and K residues. The amino acids of a tat peptide can be derivatized with biotin or similar molecule to reduce an inflammatory response.

Co-administration of a pharmacological agents means that the agents are administered sufficiently close in time for detectable amounts of the agents to present in the plasma simultaneously and/or the agents exert a treatment effect on the same episode of disease or the agents act co-operatively or synergistically in treating the same episode of disease. For example, an anti-inflammatory agent acts cooperatively with an agent including a tat peptide when the two agents are administered sufficiently proximately in time that the anti-inflammatory agent can inhibit an inflammatory response inducible by the internationalization peptide.

Statistically significant refers to a p-value that is <0.05, preferably <0.01 and most preferably <0.001.

An episode of a disease means a period when signs and/or symptoms of the disease are present interspersed by flanked by longer periods in which the signs and/or symptoms or absent or present to a lesser extent.

The CNS is used in accordance with convention to mean the brain and/or spinal cord. Ischemia or hemorrhage can affect the CNS if it occurs in the CNS, immediately proximal to the CNS, such as a subarachnoid hemorrhage or more distally within a blood vessel supplying the CNS. Ischemia or hemorrhage affects the CNS, if it of a type when left untreated, it causes detectable pathology in the CNS or a neurocognitive deficit.

In conditions such as SAH resulting from rupture, rupture is considered to occur on day 1. Thus, for example if rupture occurs on a Monday and treatment occurs within four days of rupture, treatment occurs by the end of Friday. Treatment occurring with days 5-12 post-rupture occurs within the period of Saturday to the following Friday.

The invention also provides methods of treating a damaging effect of subarachnoid hemorrhage in a population of subjects, comprising: administering an agent that inhibits binding of PSD-95 to an NMDAR2 subunit to subjects having a subarachnoid hemorrhage, wherein the damaging effect is reduced in the administered population compared to control subjects not receiving the agent. The damaging effect that is reduced can be neuronal cell death or a cognitive deficit.

DETAILED DESCRIPTION

I. General

The present application provides data from a clinical trial of a PSD-95 inhibitor in subjects undergoing endovascular repair of an aneurysm in or otherwise affecting the CNS. The subjects were stratified by whether the aneurysm ruptured before performing the endovascular surgery. Rupture is associated with higher mortality or increased debilitation if a subject survives. Outcome was assessed by number and volume of infarctions and neurocognitive measures. The trial provided evidence of significant benefit in subjects harboring an intracranial aneurysm in need of endovascular repair whether or not the aneurysm ruptured before endovascular was surgery performed, and showed minimal side effects. Surprisingly, however, the subjects benefiting most from treatment as judged both by pathology and neurocognitive outcome were those in which the aneurysm had ruptured prior to the endovascular procedure causing a subarachnoid hemorrhage. These data constitute evidence that a PSD-95 inhibitor is beneficial not only in ischemic and hemorrhagic stroke but in forms of hemorrhage in or affecting the CNS whether or not resulting from stroke including cerebral hemorrhage, intracerebral hemorrhage, intracranial hemorrhage (ICH), neurotrauma, traumatic brain injury and subdural and epidural hemorrhages, and particularly, subarachnoid hemorrhage (SAH). That treatment with a PSD-95 inhibitor is effective in both ischemic and hemorrhagic injury to the CNS, and has minimal side effects, means that such an inhibitor can be given to any subject presenting with signs of stroke or hemorrhage affecting the CNS without delaying treatment by first performing a detailed diagnostic work up, typically a brain scan, to distinguish between ischemia and hemorrhage. The trial also showed that a PSD-95 inhibitor was effective in reducing pain sometimes associated with endovascular surgery along the path of the groin puncture necessary to insert the endovascular catheters into the arterial system and traverse to its site of action, in this case, a path from the groin area to the brain area (e.g., leg, groin, abdominal area, chest, neck, and head). Although PSD-95 inhibitors have previously been reported effective in treating some forms of pain, the result that the same administration of a PSD-95 inhibitor has a dual action in inhibiting damage resulting from endovascular repair of an aneurysm and the type of pain caused by the endovascular surgery itself was not known.

II. Agents Inhibiting PSD-95

Such agents inhibit interactions between PSD-95 and one or more NMDARs, e.g., by specifically binding to PSD-95. Preferably, inhibition is of an NMDAR2 (e.g., 2A, 2B, 2C or 2D). Reference to such agents can refer to the agents alone or more typically in the case of peptide agents, the agents linked to an internalization peptide as a chimeric peptide. Such agents are useful for reducing one or more damaging effects of stroke and other neurological conditions mediated at least in part by NMDAR excitotoxicity. Such agents include peptides having an amino acid sequence including or based on the PL motif of a NMDA Receptor or PDZ domain of PSD-95. Such peptides can also inhibit interactions between PSD-95 and nNOS and other glutamate receptors (e.g., kainite receptors or AMPA receptors), such as KV1-4 and GluR6. Preferred peptides inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below.

TABLE 1

NMDA Receptors With PL Sequences

| Name | GI or Acc# | C-terminal 20mer sequence | C-terminal 4mer sequence | PL? |
|---|---|---|---|---|
| NMDAR1 | 307302 | HPTDITGPLNLSDPSVSTVV (SEQ ID NO: 13) | STVV (SEQ ID NO: 27) | X |
| NMDAR1-1 | 292282 | HPTDITGPLNLSDPSVSTVV (SEQ ID NO: 13) | STVV (SEQ ID NO: 27) | X |
| NMDAR1-4 | 472845 | HPTDITGPLNLSDPSVSTVV (SEQ ID NO: 13) | STVV (SEQ ID NO: 27) | X |
| NMDAR1-3b | 2343286 | HPTDITGPLNLSDPSVSTVV (SEQ ID NO: 13) | STVV (SEQ ID NO: 27) | X |
| NMDAR1-4b | 2343288 | HPTDITGPLNLSDPSVSTVV (SEQ ID NO: 13) | STVV (SEQ ID NO: 27) | X |
| NMDAR1-2 | 11038634 | RRAIEREEGQLQLCSRHRES (SEQ ID NO: 14) | HRES (SEQ ID NO: 28) | |
| NMDAR1-3 | 11038636 | RRAIEREEGQLQLCSRHRES (SEQ ID NO: 14) | HRES (SEQ ID NO: 28) | |
| NMDAR2C | 6006004 | TQGFPGPCTWRRISSLESEV (SEQ ID NO: 15) | ESEV (SEQ ID NO: 29) | X |
| NMDAR3 | 560546 | FNGSSNGHVYEKLSSIESDV (SEQ ID NO: 11) | ESDV (SEQ ID NO: 12) | X |
| NMDAR3A | 17530176 | AVSRKTELEEYQRTSRTCES (SEQ ID NO: 16) | TCES (SEQ ID NO: 30) | |
| NMDAR2B | 4099612 | FNGSSNGHVYEKLSSIESDV (SEQ ID NO: 11) | ESDV (SEQ ID NO: 12) | X |
| NMDAR2A | 558748 | LNSCSNRRVYKKMPSIESDV (SEQ ID NO: 17) | ESDV (SEQ ID NO: 12) | X |
| NMDAR2D | 4504130 | GGDLGTRRGSAHFSSLESEV (SEQ ID NO: 18) | ESEV (SEQ ID NO: 29) | X |
| Glutamate receptor delta 2 | AF009014 | QPTPTLGLNLGNDPDRGTSI (SEQ ID NO: 19) | GTSI (SEQ ID NO: 31) | X |
| Glutamate receptor 1 | I28953 | MQSIPCMSHSSGMPLGATGL (SEQ ID NO: 20) | ATGL (SEQ ID NO: 32) | X |
| Glutamate receptor 2 | L20814 | QNFATYKEGYNVYGIESVKI (SEQ ID NO: 21) | SVKI (SEQ ID NO: 33) | X |
| Glutamate receptor 3 | AF167332 | QNYATYREGYNVYGTESVKI (SEQ ID NO: 22) | SVKI (SEQ ID NO: 33) | X |
| Glutamate receptor 4 | U16129 | HTGTAIRQSSGLAVIASDLP (SEQ ID NO: 23) | SDLP (SEQ ID NO: 34) | X |
| Glutamate receptor 5 | U16125 | SFTSILTCHQRRTQRKETVA (SEQ ID NO: 24) | ETVA (SEQ ID NO: 35) | X |
| Glutamate receptor 6 | U16126 | EVINMHTFNDRRLPGKETMA (SEQ ID NO: 25) | ETMA (SEQ ID NO: 36) | X |

Some peptides inhibit interactions between PSD-95 and multiple NMDAR subunits. In such instances, use of the peptide does not necessarily require an understanding of the respective contributions of the different NMDARs to excitatory neurotransmission. Other peptides are specific for a single NMDAR.

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T/]-[D/E/Q/N]-[V/L] (SEQ ID NO:38) at their C-terminus. Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides have an amino acid sequence comprising or consisting of KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide)

are preferred. In some such peptides, all amino acids are from the C-terminus of an NMDA receptor (not including amino acids from an internalization peptide). The invention also includes peptidomimetics of these and other peptides disclosed herein.

Other peptides that inhibit interactions between PDS95 and NDMARs include peptides from PDZ domain 1 and/or 2 of PSD-95 or a subfragment of any of these that inhibits interactions between PSD-95 and an NMDA receptor, such as NR2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1): 71-82 (1997) (human sequence) or NP_031890.1, GI:6681195 (mouse sequence) or corresponding regions of other species variants.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3,4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 has described a series of analogs of NR2B9c. PDZ-binding activity is exhibited by peptides having only three C-terminal amino acids (SDV). Bach also reports analogs having an amino acid sequence comprising or consisting of $X_1tSX_2V$ (SEQ ID NO:7), wherein t and S are alternative amino acids, $X_1$ is selected from among E, Q, and A, or an analogue thereof, $X_2$ is selected from among A, Q, D, N, (N-Methyl)-A, (N-methyl)-Q, (N-methyl)-D, and (N-methyl)-N or an analogue thereof. Optionally the peptide is N-alkylated in position P3 position (third amino acid from C-terminus, i.e. position occupied by tS). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseisslk-rrrqrrkkrgyin (SEQ ID NO:8) (lower case letters indicating D amino acids), and reports it to be effective inhibiting cerebral ischemia. Another effect peptide described herein is Rv-Tat-NR2B9c (RRRQR-RKKRGYKLSSIESDV; SEQ ID NO:9).

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. Int. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:10) from the C-terminus of NMDAR2B was effective in inhibiting binding of NMDAR2B to PSD-95. IETDV (SEQ ID NO:73) can also be used instead of IESDV as can peptides comprising IESDV or IESTDV. Optionally, about 2-10 copies of a PEG can be joined in tandem as a linker. Optionally, the linker can also be attached to an internalization peptide or lipidated to enhance cellular uptake. Examples of illustrative dimeric inhibitors are shown below (see Bach et al., PNAS 109 (2012) 3317-3322). Any of the PSD-95 inhibitors disclosed herein can be used instead of IETDV, and any internalization peptide or lipidating moiety can be used instead of tat in the configurations shown below. Other linkers to that shown can also be used.

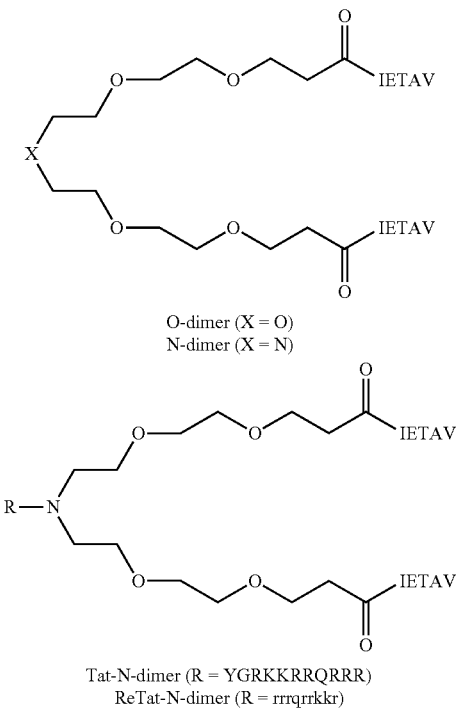

O-dimer (X = O)
N-dimer (X = N)

Tat-N-dimer (R = YGRKKRRQRRR)
ReTat-N-dimer (R = rrrqrrkkr)

N = nitrogen, O = Oxygen

IETAV is assigned SEQ ID NO:74, YGRKKRRQRRR SEQ ID NO:2, and rrrqrrkkr, SEQ ID NO:75, lower case letters indicated D-amino acids.

Appropriate pharmacological activity of peptides, peptidomimetics or other agent can be confirmed if desired, using previously described rat models of stroke before testing in the primate and clinical trials described in the present application. Peptides, peptidomimetics or other agents can also be screened for capacity to inhibit interactions between PSD-95 and NMDAR2B using assays described in e.g., US 20050059597, which is incorporated by reference. Useful peptides, peptidomimetics or other agents typically have IC50 values of less than 50 µM, 25 µM, 10 µM, 0.1 µM or 0.01 µM in such an assay. Preferred peptides typically have an IC50 value of between 0.001-1 µM, and more preferably 0.05-0.5 or 0.05 to 0.1 µM. When a peptide, peptidomimetic or other agent is characterized as inhibiting binding of one interaction, e.g., PSD-95 interaction to NMDAR2B, such description does not exclude that the peptide or agent also inhibits another interaction, for example, inhibition of PSD-95 binding to nNOS.

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Pharmacological agents also include small molecules that inhibit interactions between PSD-95 and NMDAR2B, and/or other interactions described above. Suitable small-molecule inhibitors are described in WO/2009/006611. An exemplary class of suitable compounds are of the formula:

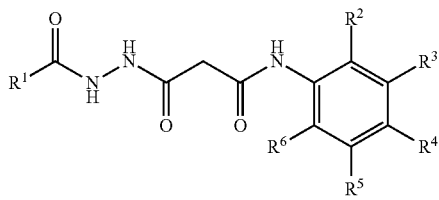

wherein $R^1$ is a member selected from the group consisting of cyclohexyl substituted with 0-4 $R^7$, phenyl substituted with 0-4 $R^7$, —$(CH_2)_u$—$(CHR^8R^9)$, a branched $C_{1-6}$ alkyl(isopropyl, isobutyl, 1-isopropyl-2-methyl-butyl, 1 ethyl-propyl), and —NH—C(O)—$(CR^{10}R^{11})_v$H;

each $R^7$ is independently a member selected from the group consisting of $C_{1-6}$ alkyl, $C_{1-6}$ alkoxy, —C(O)$R^{12}$, OH, COOH, —NO, N-substituted indoline and a cell membrane translocation peptide;

each $R^8$ and $R^9$ is independently selected from the group consisting of H, OH, cyclohexane, cyclopentane, phenyl, substituted phenyl and cyclopentadiene;

each $R^{10}$ and $R^{11}$ is independently selected from the group consisting of H, cyclohexane, phenyl and a cell membrane translocation peptide;

$R^{12}$ is a member selected from the group consisting of $C_{1-6}$ alkyl and aryl; and each of u and v are independently from 0 to 20;

wherein one of $R^2$, $R^3$, $R^4$, $R^5$ and $R^6$ is —COOH, and wherein the remainder of $R^2$, $R^3$, $R^4$, $R^5$ and $R^6$ are each independently selected from the group consisting of F, H, $OCH_3$ and $CH_3$.

One such compound is 0620-0057, the structure of which is:

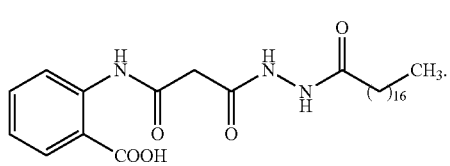

0620-0057

A pharmacological agent can be linked to an internalization peptide to facilitate uptake into cells and/or across the blood brain barrier. Any of the above pharmacological agents can be linked to any of the internalization peptides described below. Internalization peptides are a well-known class of relatively short peptides that allow many cellular or viral proteins to traverse membranes. Internalization peptides, also known as cell membrane transduction peptides or cell penetrating peptides can have e.g., 5-30 amino acids. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and *Pseudomonas aeruginosa* exotoxin A (ETA). Other examples are described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005, Gao, ACS Chem. Biol. 2011, 6, 484-491, SG3 (RLSGMNEVLSFRWL) (all incorporated by reference).

A preferred internalization peptide is tat from the HIV virus. A tat peptide reported in previous work comprises or consists of the standard amino acid sequence YGRKKRRQRRR (SEQ ID NO:2) found in HIV Tat protein. Thus two preferred agents incorporating this tat peptide are the peptides comprising or consisting of the amino acid sequence YGRKKRRQRRRKLSSIESDV, SEQ ID NO:6 (also known as Tat-NR2B9c or TAT-NR2B9C) or YGRKKRRQRRRKLSSIETDV (SEQ ID NO:37). If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)$_4$ (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRKKRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present. Other tat peptides that can be used include GRKKRRQRRRPQ (SEQ ID NO:4) and GRKKRRQRRRP (SEQ ID NO:26).

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRKKRRQRRR (SEQ ID NO:3) is preferred. Another preferred variant tat peptide consists of GRKKRRQRRR (SEQ ID NO:1). Another preferred tat peptide comprises or consists of RRRQRRKKRG or RRRQRRKKRGY (amino acids 1-10 or 1-11 of SEQ ID NO:9). Other tat derived peptides that facilitate uptake of a pharmacological agent without inhibiting N-type calcium channels include those presented in Table 2 below.

TABLE 2

| | |
|---|---|
| X-FGRKKRRQRRR (F-Tat) | (SEQ ID NO: 69) |
| X-GKKKKQKKK | (SEQ ID NO: 50) |
| X-RKKRRQRRR | (SEQ ID NO: 51) |
| X-GAKKRRQRRR | (SEQ ID NO: 52) |
| X-AKKRRQRRR | (SEQ ID NO: 53) |
| X-GRKARRQRRR | (SEQ ID NO: 54) |
| X-RKARRQRRR | (SEQ ID NO: 55) |
| X-GRKKARQRRR | (SEQ ID NO: 56) |
| X-RKKARQRRR | (SEQ ID NO: 57) |
| X-GRKKRRQARR | (SEQ ID NO: 58) |
| X-RKKRRQARR | (SEQ ID NO: 59) |
| X-GRKKRRQRAR | (SEQ ID NO: 60) |
| X-RKKRRQRAR | (SEQ ID NO: 61) |
| X-RRPRRPRRPRR | (SEQ ID NO: 62) |
| X-RRARRARRARR | (SEQ ID NO: 63) |
| X-RRRARRRARR | (SEQ ID NO: 64) |
| X-RRRPRRRPRR | (SEQ ID NO: 65) |
| X-RRPRRPRR | (SEQ ID NO: 66) |
| X-RRARRARR | (SEQ ID NO: 67) |

X can represent a free amino terminus, one or more amino acids, or a conjugated moiety. Internalization peptides can be used in inverso or retro or inverso retro form with or without the linked peptide or peptidomimetic being in such form. For example, a preferred chimeric peptide has an amino acid sequence comprising or consisting of RRRQRRKKRGY-KLSSIESDV (SEQ ID NO:9) or having an amino acid sequence comprising or consisting of RRRQRRKKRGY-KLSSIETDV (SEQ ID NO:37).

Internalization peptides can be attached to pharmacological agents by conventional methods. For example, the agents can be joined to internalization peptides by chemical linkage, for instance via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio)propionate (SPDP) or N,N'-(1,3-phenylene)bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1, 4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Instead of or as well as linking a peptide (or other agent) inhibiting PSD-95 to an internalization peptide, such a peptide can be linked to a lipid (lipidation) to increase hydrophobicity of the conjugate relative to the peptide alone and thereby facilitate passage of the linked peptide across cell membranes and/or across the brain barrier. Lipidation is preferably performed on the N-terminal amino acid but can also be performed on internal amino acids, provided the ability of the peptide to inhibit interaction between PSD-95 and NMDAR 2B is not reduced by more than 50%. Preferably, lipidation is performed on an amino acid other than one of the four most C-terminal amino acids. Lipids are organic molecules more soluble in ether than water and include fatty acids, glycerides and sterols. Suitable forms of lipidation include myristoylation, palmitoylation or attachment of other fatty acids preferably with a chain length of 10-20 carbons, such as lauric acid and stearic acid, as well as geranylation, geranylgeranylation, and isoprenylation. Lipidations of a type occurring in posttranslational modification of natural proteins are preferred. Lipidation with a fatty acid via formation of an amide bond to the alpha-amino group of the N-terminal amino acid of the peptide is also preferred. Lipidation can be by peptide synthesis including a prelipidated amino acid, be performed enzymatically in vitro or by recombinant expression, by chemical crosslinking or chemical derivatization of the peptide. Amino acids modified by myristoylation and other lipid modifications are commercially available.

Lipidation preferably facilitates passage of a linked peptide (e.g., KLSSIETDV (SEQ ID NO:5), or KLSSIETDV (SEQ ID NO:43)) across a cell membrane and/or the blood brain barrier without causing a transient reduction of blood pressure as has been found when a standard tat peptide is administered at high dosage (e.g., at or greater than 3 mg/kg), or at least with smaller reduction that than the same peptide linked to a standard tat peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

III. Agents and Methods for Reperfusion

Treatment of ischemic strokes with a PSD-95 inhibitor can be combined with reperfusion therapy. Such reperfusion can be achieved using the intravenous or intra-arterial administration of thrombolytic agents such as tPA, streptokinase or urokinase, by using mechanical means to re-open blocked arteries, or by other means to enhance the collateral circulation to an ischemic brain area. By administering the PSD-95 inhibitor, there is more time available to perform a brain scan to determine presence of ischemic stroke, and then administer tPA or administer another reperfusion therapy if appropriate. Thus, more subjects with ischemic stroke can benefit from tPA treatment or from another therapy that enhances brain reperfusion and at the same time benefit from treatment with a PSD-95 inhibitor.

Plaques, blood clots or any other particulate matter (collectively known as emboli) causing ischemia can be dissolved removed or bypassed by both pharmacological and physical means. The dissolving, removal of emboli or other obstructions to blood flow and consequent restoration of blood flow is referred to as reperfusion. One class of agents acts by thrombolysis. These agents work by stimulating fibrinolysis by plasmin through infusion of tissue plasminogen activator (tPA). Plasmin clears cross-linked fibrin mesh (the backbone of a clot), making the clot soluble and subject to further proteolysis by other enzymes, and restores blood flow in occluded blood vessels. Examples of thrombolytic agents include tissue plasminogen activator t-PA, alteplase (Activase®), reteplase (Retavase®), tenecteplase (TNKase®), anistreplase (Eminase®), streptokinase (Kabikinase®, Streptase®), and urokinase (Abbokinase®).

Another class of drugs that can be used for reperfusion is vasodilators. These drugs act by relaxing and opening up blood vessels thus allowing blood to flow around an obstruction. Some examples of types of vasodilators alpha-adrenoceptor antagonists (alpha-blockers), Angiotensin receptor blockers (ARBs), Beta$_2$-adrenoceptor agonists ($\beta_2$-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, and renin inhibitors Mechanical methods of reperfusion include angioplasty, catheterization, and artery bypass graft surgery, stenting, embolectomy, or endarterectomy. Such procedures restore plaque flow by mechanical removal of a plaque, holding a blood vessel open, so blood can flow around a plaque or bypassing a plaque. Other methods of enhancing reperfusion include adjunctive devices such as intra-aortic balloons (Co-Axia NeuroFlo™) that divert the cardiac output of blood to the cerebral circulation, thereby increasing collateral perfusion to the ischemic area (see clinicaltrials.gov/ct2/show/NCT00119717).

IV. Stroke

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. In some instances, strokes may arise due to multiple emboli, or due to a generalized arteriopathy. In the former, the emboli may arise from the heart, such as in the case of endocarditis, atrial fibrillation, or cardiac valvular disease. In the latter, the arteriopathy may comprise an arteritis (an infectious or autoimmune inflammation of the arteries). In such instances, multiple strokes may arise in the brain, sometimes due to many small emboli. In such instances, another means to measure the extent of pathological damage resulting from stroke is to count the number of ischemic lesions. This applies especially in the case of procedurally-induced strokes, such as strokes incurred after endovascular repair of brain aneurysm. In this instance, the intravascular manipulation may liberate multiple emboli that can produce many strokes in the brain. The symptomatic effect depends both on the volume of an infarction, the number of infarctions and where in the brain it/they is/are located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a subject as follows.

TABLE 3

| | |
|---|---|
| 0 | No symptoms at all |
| 1 | No significant disability despite symptoms; able to carry out all usual duties and activities. |
| 2 | Slight disability; unable to carry out all previous activities but able to look after own affairs without assistance. |
| 3 | Moderate disability requiring some help, but able to walk without assistance |
| 4 | Moderate to severe disability; unable to walk without assistance and unable to attend to own bodily needs without assistance. |
| 5 | Severe disability; bedridden, incontinent, and requiring constant nursing care and attention. |

The Barthel Index is based on a series of questions about the subject's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf.

The scale is based on the ability of a subject to carry out 11 groups of functions that include assessments of the subject's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke. Another cause of blood clots is the intravascular stasis of blood due to vascular lesions such as brain aneurysms, due to the intravascular introduction of endovascular tools, or due to thrombosis due to the intravascular introduction of endovascular tools.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms. Subjects undergoing heart surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Ischemic stroke can also transform in to hemorrhagic stroke as a result of reperfusion. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke in one part of the brain can lead to ischemic stroke in another through shortage of blood lost in the hemorrhagic stroke.

In patients with unruptured aneurysms, strokes that are procedurally-related arise either as a result of emboli being dislodged by the endovascular surgery (most common), or due to other complications of the endovascular surgery, such as perforation of the aneurysm (producing a hemorrhagic stroke) or inadvertent occlusion of a parent vessel due to mis-placement of endovascular coils or stents, or inadvertent occlusion of a parent vessel due to injury to the vessel that results in thrombosis, dissection, or perforation.

In patients with ruptured aneurysms whose aneurysms are treated by endovascular means, strokes that are procedurally-related can arise for the same reasons as in patients with unruptured aneurysms. However, such patients can also sustain additional ischemic or hemorrhagic brain injury because ruptured aneurysms are more fragile than unruptured ones, so the risk of the aneurysm rupturing before or during the procedure is higher. Additional injury can result from increased intracranial pressure due to the original aneurysm rupture causing brain swelling (edema), or due to the intracerebral accumulation of the leaking blood, or both, or delayed ischemia due to the phenomenon of "vasospasm". In subarachnoid hemorrhage the risk of vasospasm is greatest between days 5-12 after the aneurysm rupture, and is the result of vasoactive substances being released by the blood clot that surrounds the brain arteries. Vasospasm can be responsible for delayed ischemic strokes in such patients. Damage can also arise from alterations in cerebral blood flow due to loss of cerebral vascular autoregulation from a sudden rise of intracranial pressure immediately following the rupture.

V. Subjects Amenable to Treatment

The clinical trial provides evidence that a PSD-95 inhibitor is effective in reducing infarcts and neurocognitive deficits in subjects undergoing endovascular repair of both unruptured and ruptured aneurysms. Subjects with an unruptured aneurysm are predominantly at risk of ischemic stroke or subarachnoid hemorrhage. Subjects with ruptured aneurysms are also at risk of ischemic stroke but have added risk of hemorrhagic stroke, particularly from subarachnoid hemorrhage. Because of the added risk of hemorrhagic stroke, subjects with ruptured aneurysms have the greatest risk of death or debilitating injury as result of the aneurysm. Surprisingly, the present data shows that these patients derive the greatest benefit from a PSD-95 inhibitor determined by both pathology (number and volume of infarcts) and neurocognitive testing. These results indicate not only that a PSD95 inhibitor can be used to treat ischemic or hemorrhagic stroke but provide evidence that such an inhibitor can be used for treatment of subjects with hemorrhages in or otherwise affecting the CNS, whether or not resulting from stroke. This is surprising because PSD-95 inhibitors have generally been thought to act though the reduction of ischemia, leading to better outcomes. In SAH, PSD-95 inhibitors such as Tat-NR2B9c were given within 72 hours of rupture, when generally no ischemia is present, yet showed benefit. Ischemia in SAH patients generally occurs after vasospasm, and generally presents between day 5 and day 12 post rupture. Tat-NR2M9c has a short half life in plasma (about 20 minutes) and a short half-life in the brain (about 5 hours), suggesting TAT-NR2B9c acts at least in part through a different mechanism than reducing ischemia to provide the benefit observed in the examples below. However, practice of the invention is not dependent on an understanding of mechanism.

The most common hemorrhages in or otherwise affecting the CNS are cerebral hemorrhage, intracerebral hemorrhage, intracranial hemorrhage (ICH) (each occurring inside the brain), and subdural and epidural hemorrhages, and subarachnoid hemorrhage (SAH) (each occurring inside the skull but outside the brain itself). These hemorrhages are referred to as being a hemorrhagic stroke if they occur spontaneously as when aneurysm ruptures or a blood vessel leaks from hypertension, or drugs such as anti-coagulants or cocaine, but are referred to simply as hemorrhage if they are from physical trauma, such as a fall, blow or shaken baby syndrome. The present methods are particularly suitable for treatment of subarachnoid hemorrhage because this form of hemorrhage was present in the subjects deriving greatest benefit from the clinical trial.

Subjects amenable to treatment include subjects presenting with signs(s) and/or symptom(s) of ischemia or hemorrhage either in the CNS or immediately proximate thereto as in the case of a subarachnoid, subdural or epidural hemorrhage or elsewhere in the body but still otherwise affecting the CNS as when affecting a blood vessel whose obstruction may impede blood flow through the brain, or in which hemorrhage may cause injury through edema, pressure of accumulating blood or otherwise. These subjects include subjects presenting with sign(s) and/or symptoms of stroke, myocardial ischemia, pulmonary embolism, limb ischemia, renal, or retinal ischemia or hemorrhage in or proximate to the brain (e.g., subarachnoid hemorrhage). Such subjects include subjects in which such a condition is suspected but other conditions cannot be excluded, as well as subjects who have been diagnosed according to generally recognized criteria, e.g., DSM IV TR.

Subjects amenable to treatment also include subjects at risk of ischemia or hemorrhage but in which onset of ischemia or hemorrhage has not yet occurred. A subject is at risk if he or she has a higher risk of developing ischemia or hemorrhage than a control population. The control population may include one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of transient cerebral ischemic attack because the frequency of transient cerebral ischemic attack is increased in a population of subjects who have undergone heart surgery as compared to a population of subjects who have not.

Subjects at risk of ischemia in or affecting the CNS include those undergoing a surgical procedure on the brain or CNS, such as endovascular surgery, clipping, stenting or microcathetherization. Such subjects also include those undergoing surgery elsewhere in the body that affects a blood vessel supplying the brain (that is connecting the brain to the heart, for example, carotid arteries and jugular veins) or on an artery supplying blood to the retina, kidney, spinal cord or limbs. Subjects at risk of hemorrhage affecting the CNS also including those undergoing a surgical procedure on the brain. Other subjects at risk include those having had an injury to the head such as fall or blow, or have been subject to sudden changes in velocity, such as in shaken baby syndrome or a traffic accident. Other subjects at risk of hemorrhage are those with hypertension, clotting disorders, arteriovenous malformation or aneurysm. A preferred class of subjects are those undergoing endovascular surgery to treat a brain aneurysm with or without rupture.

VI. Combined Methods of Treatment

For ischemic indications, a PSD-95 inhibitor and a form of reperfusion can be administered to a subject amenable to treatment (see U.S. 61/501,117, filed Jun. 24, 2011, incorporated by reference for all purposes). The PSD-95 inhibitor and reperfusion can be administered in either order or at the same time. Usually, the PSD-95 inhibitor and reperfusion are administered at the same, overlapping or proximate times (i.e., within a 15 minutes interval) or the PSD-95 inhibitor is administered first.

For treatment of ischemias that cannot be predicted in advance, the PSD-95 inhibitor can be administered as soon as practical after onset of ischemia. For example, the PSD-95 inhibitor can be administered within a period of 0.5, 1, 2, 3, 4, 5 or 6, 12 or 24 hours or such other time as there remains sufficient collateral circulation to maintain an ischemic penumbra after onset of ischemia. For ischemias or hemorrhage that can be predicted in advance, or are potential causes of symptoms, the PSD-95 inhibitor can be administered before, concurrent with or after onset of ischemia. For example, for an ischemia or hemorrhage resulting from surgery, the PDS95 is sometimes routinely administered in a period starting 30 minutes before beginning surgery and ending one hour after surgery without regard to whether ischemia has or will develop. Because the PSD-95 inhibitor is free of serious side effects, it can be administered when stroke, hemorrhage or other ischemic condition are suspected without a diagnosis according to art-recognized criteria having been made. For example, the PSD-95 inhibitor can be administered in an ambulance transporting a subject to a hospital. The PSD-95 inhibitor can also be safely administered to a subject at risk of stroke or other ischemic condition or hemorrhagic condition before onset who may or may not actually develop the condition. The PSD-95 inhibitor can also be administered in the operating room or endovascular suite to an anesthetized patient on the presumptive diagnosis of ongoing or impending brain ischemia or other injury.

Following, or sometimes before, administration of the PSD-95 inhibitor, a subject presenting with sign(s) and/or symptom(s) of ischemia can be subject to further diagnostic assessment to determine whether the subject has ischemia within or otherwise affecting the CNS and determine whether the subject has or is susceptible to hemorrhage. Most particularly in subjects presenting with symptoms of stroke or other acute disorder affecting the CNS, testing attempts to distinguish whether the subject has a hemorrhage. Diagnostic tests can include a scan of one or more organs, such as a CAT scan, MRI or PET imaging scan. The organ(s) scanned include any suspected as being the site of ischemia (e.g., brain, heart, limbs, spine, lungs, kidney, retina) as well as any otherwise suspect of being the source of a hemorrhage. A scan of the brain is the usual procedure for distinguishing between ischemic and hemorrhagic conditions. Diagnostic assessment can also include taking or reviewing a subject's medical history and performing other tests. Presence of any of the following factors alone or in combination can be used in assessing whether reperfusion therapy presents an unacceptable risk: subject's symptoms are minor or rapidly improving, subject had seizure at onset of stroke, subject has had another stroke or serious head trauma within the past 3 months, subject had major surgery within the last 14 days, subject has known history of intracranial hemorrhage, subject has sustained systolic blood pressure >185 mmHg, subject has sustained diastolic blood pressure >110 mmHg, aggressive treatment is necessary to lower the subject's blood pressure, subject has symptoms suggestive of subarachnoid hemorrhage, subject has had gastrointestinal or urinary tract hemorrhage within the last 21 days, subject has had arterial puncture at noncompressible site within the last 7 days, subject has received heparin with the last 48 hours and has elevated PTT, subject's prothrombin time (PT) is >15 seconds, subject's platelet count is <100,000 µL subject's serum glucose is <50 mg/dL or >400 mg/dL subject is a hemophiliac or has other clotting deficiencies.

The further diagnostic investigation determines according to recognized criteria or at least with greater probability that before the investigation whether the subject has an ischemic condition, and whether the subject has a hemorrhage, has an unacceptable risk of hemorrhage or is otherwise excluded from receiving reperfusion therapy due to unacceptable risk of side effects. Subjects in which a diagnosis of an ischemic conditions within or otherwise likely to affect the CNS is confirmed who are without unacceptable risk of side effects can then be subject to reperfusion therapy. Preferably, reperfusion therapy is performed as soon as practical after completion of any diagnostic procedures. In some subjects, reperfusion therapy is commenced more than 1, 2, 3, 4, 4.5, 5, 6, 7, 8, 10, 12, 15, 18, or 24 hr after onset of ischemia. In some subjects, reperfusion therapy is commenced 1-6, 1-12, 1-18 or 1-24 hr after onset of ischemia. In some subjects, reperfusion therapy is commenced outside the usual 3-4.5 hr window in which reperfusion therapy has hitherto been considered to effective. For example in some subjects, reperfusion therapy is commenced more than 3 hours or more than 4.5 hours after onset of ischemia and up to 24 or 48 hours after onset of ischemia. In some subjects, reperfusion therapy is commenced, after 5, 6, 7, 8, 9 or 10 hours and up to 24 or 48 hours after onset of ischemia. In some subjects, reperfusion therapy is comments from 275-390 minutes after onset of ischemia.

The time of reperfusion can also be measured from the administration of the PSD-95 inhibitor. The interval can be, for example, 5 minutes to 24 hours. The interval may be for example, 30 minutes to 6 hours or 1-3 hours.

Subjects in which an ischemic condition is not confirmed or is considered unlikely are not usually administered reperfusion therapy, particularly pharmacological reperfusion therapy. Subjects in which an ischemic condition is confirmed or considered likely but are considered at unacceptable risk of side effects from pharmacological reperfusion therapy are not administered pharmacological reperfusion therapy. Such subjects may have obtained benefit of the PSD-95 inhibitor but are spared the risk of unacceptable side effects from reperfusion therapy.

Both treatment with a PSD-95 inhibitor and reperfusion therapy independently have ability to reduce infarction size and functional deficits due to ischemia. When used in combination, the reduction in infarction size and/or functional deficits is preferably greater than that from use of either agent alone administered under a comparable regime other than for the combination. More preferably, the reduction in infarction side and/or functional deficits is at least additive or preferably more than additive of reductions achieved by the agents alone under a comparable regime except for the combination. In some regimes, the reperfusion therapy is effective in reducing infarction size and/or functional times at a time post onset of ischemia (e.g., more than 4.5 hr) when it would be ineffective but for the concurrent or prior administration of the PSD-95 inhibitor. Put another way, when a subject is administered a PSD-95 inhibitor and reperfusion therapy, the reperfusion therapy is preferably at least as effective as it would be if administered at an earlier time without the PSD-95 inhibitor. Thus, the PSD-95 inhibitor effectively increases the efficacy of the reperfusion therapy by reducing one or more damaging effects of ischemia before or as reperfusion therapy takes effects. The PSD-95 inhibitor can thus compensate for delay in administering the reperfusion therapy whether the delay be from delay in the subject recognizing the danger of his or her initial symptoms delays in transporting a subject to a hospital or other medical institution or delays in performing diagnostic procedures to establish presence of ischemia and/or absence of hemorrhage or unacceptable risk thereof. Statistically significant combined effects of PSD-95 inhibitor and reperfusion therapy including additive or synergistic effects can be demonstrated between populations in a clinical trial or between populations of animal models in preclinical work.

Subjects in which hemorrhage in or otherwise affecting the CNS is confirmed, or cannot be excluded with acceptable assurance to the physician are not usually administered pharmacological reperfusion therapy but can be subject to other combination treatments, both surgical and pharmacological. Treatment with anti-PSD-95 inhibitors can also take place in combination with other drugs, treatments or interventions useful for indications associated with hemorrhages in or otherwise affecting the CNS, including SAH and ICH. Hemorrhages in or otherwise affecting the CNS can be treated by surgical intervention, and depending on the diagnosis, therapeutics or treatments, such as for example, antihypertensive medications, FactorVIIa or other clotting or coagulation factors, mannitol or other drugs to raise intracranial pressure, acetaminophen or other NSAIDs to reduce headaches and avoid hyperthermia, frozen plasma, vitamin K, protamine, platelet transfusions, fosphenyloin or anticonvulsants if seizures are present or for lobar hemorrhage, H2 antagonists or proton pump inhibitors for stress ulcer prophylaxis linked to ICH, or corticosteroids to reduce swelling. Because no safety or drug related interactions were observed in a human clinical trial of the PSD-95 inhibitor Tat-NR2B9c, such combination treatments are expected to be effective.

In other methods, in which a subject having or at risk of ischemia in or otherwise affecting the CNS, a subject is administered a PSD95 inhibitor without co-administration of other pharmacological treatment to treat or effect prophylaxis of the ischemia. In some methods, such a subject is administered a PSD95 inhibitor without administering other pharmacological treatment to treat or effect prophylaxis of ischemia and without performing mechanical reperfusion therapy. In some methods, a subject having or at risk of a hemorrhage in or otherwise affecting the CNS is administered as PSD95 inhibitor without any other pharmacological treatment to treat or effect prophylaxis of the hemorrhage.

VI. Effective Regimes of Administration

A PSD-95 inhibitor is administered in an amount, frequency and route of administration effective to reduce, inhibit or delay one or more damaging effects of ischemia or hemorrhage on the CNS and preferably pain associated with either the ischemia or hemorrhage or surgical treatment thereof. Unless otherwise indicated dosages for inhibitors that are chimeric agents including a pharmacologic agent linked to an internalization peptide refer to the whole agent rather than just the pharmacological agent component of the chimeric agent. An effective amount means an amount of agent sufficient significantly to reduce, inhibit or delay onset or more damaging effects of ischemia or hemorrhage and preferably pain as well in a population of subjects (or animal models) suffering from the disease treated with an agent of the invention relative to the damage in a control population of subjects (or animal models) suffering from that disease or condition who are not treated with the agent. The control population can be contemporaneously treated with a placebo or can be a historical control. The amount is also considered effective if an individual treated subject achieves an outcome more favorable than the mean outcome in a control population of comparable subjects not treated by methods of the invention. An effective regime involves the administration of an effective dose at a frequency and route of administration needed to achieve the intended purpose.

The outcome of treating stroke or hemorrhage affecting the CNS can be determined by infarction volume, number of infarctions, or disability index. A regime can be recognized as effective if an individual treated subject shows a disability of two or less on the Rankin scale and 75 or more on the Barthel scale, see Lees et al., N. Engl. J. Med. 354:588-600 (2006) or if a population of treated subjects shows a significantly improved (i.e., less disability) distribution of scores on any stroke, disability or other appropriate scale (e.g., Barthel, Rankin, NIH Stroke Scale) than a comparable untreated population, or if a population of treated subjects shows significantly reduced infarction size or number compared with a comparable untreated population. A single dose of agent is usually sufficient for treatment of stroke.

Infarctions in a clinical trial or individual patient are preferably assessed by MRI, particularly FLAIR (fluid attenuated inversion recovery) and/or DWI (diffusion weighted imaging). FLAIR is more sensitive but DWI is more specific for new infarctions. Identification of infarctions present at the same spatial location by both FLAIR and DWI provide a sensitive and selective detection of new infarctions resulting from a current episode of stroke or hemorrhage. Other MRI sequences can be used alone or in combination with DWI and/or FLAIR.

Depending on the agent, administration can be parenteral, intravenous, nasal, oral, subcutaneous, intra-arterial, intracranial, intrathecal, intraperitoneal, topical, intranasal or intramuscular. Intravenous administration is preferred for peptide agents.

For chimeric agents including an internalization peptide, particularly a HIV tat peptide comprising the amino acid sequence, administration of the agent may or may not be combined with an anti-inflammatory agent to reduce release or histamine and its downstream effects associated with high levels of the internalization peptide. Preferred agents for co-administration are inhibitors of mast cell degranulation, such as cromolyn or lodoxamide or any others listed herein. Antihistamines or corticosteroids can also be used, particularly in combinations or higher dosages (see WO2009/076105, and WO2010/14474261).

For administration to humans, a preferred dose of the chimeric agent Tat-NR2B9c is 2-3 mg/kg and more preferably 2.6 mg/kg. Indicated dosages should be understood as including the margin of error inherent in the accuracy with which dosages can be measured in a typical hospital setting. The dose is preferred because it is the maximum dose with which the agent can be administered without release of significant amounts of histamine and the ensuing sequelae in most subjects. Although release of histamine at higher dosages can be controlled by co-administration of an anti-inflammatory as discussed above and in any event usually spontaneously resolves without adverse events, it is best avoided by keeping the dose below 3 mg/kg and preferably at 2-3 mg/kg, more preferably 2.6 mg/kg. Another preferred dose level is 1-3 mg/kg, e.g., 1.5 mg/kg. Such amounts can be for single dose administration, i.e., one dose per episode of disease, or multiple dose administration.

The dosages indicated above are for the chimeric agent Tat-NR2B9c (YGRKKRRQRRRKLSSIESDV; SEQ ID NO:6). Equivalent dosages for other agents to achieve the same effect can be determined by several approaches. For close variants of that agent in which one or a few amino acids are substituted, inserted or deleted and the molecular weight remains the same within about +/−25%, the above dosages are still a good guide. However, in general, for other agents, equivalent dosages can vary depending on the molecular weight of the agent with and without internalization peptide if present, its Kd for its target, and its pharmacokinetic and pharmacodynamic parameters. For some agents, equivalent dosages can be calculated so as to deliver an equimolar amount of the pharmacological agent. For other agent, further adjustment is made to account for differences in Kd or pharmacokinetic or pharmacodynamic parameters. For some agents, equivalent dosages are determined empirically from the dose achieved to reach the same endpoint in an animal model or a clinical trial.

Peptide agents, such as Tat-NR2B9c are preferably delivered by infusion into a blood vessel, more preferably by intravenous infusion. For the chimeric agent Tat-NR2B9c, a preferred infusion time providing a balance between these considerations is 5-15 minutes and more preferably 10 min. Indicated times should be understand as including a marking of error of +/−10%. Infusion times do not include any extra time for a wash out diffusion to wash out any remaining droplets from an initial diffusion that has otherwise proceeded to completion. The infusion times for Tat-NR2B9c can also serve as a guide for other pharmacological agents, optionally linked to internalization peptides, particularly close variants of Tat-NR2B9c, as discussed above.

Multi-dose regimes of Tat-NR2B9c or other PSD95 inhibitor can also be used. For example, multi-dose regimes can be used for treating subarachnoid hemorrhage or other hemorrhages of the CNS. Multi-dose regimes can involve administering a PSD95 inhibitor once or twice a day (or more) for up to 12 days starting on the day of hemorrhage. In one preferred regime, the inhibitor is administered once a day for at least three days. In another preferred regime, the inhibitor is administered twice a day for at least two days. In some regimes, at least one dose is administered within 4 days of rupture (i.e., on or before day 4 with rupture being on day 1). In some regimes, a dose is administered on day 5 or later after rupture. In some regimes, a dose is administered on any or all of days 1-4 and another dose on any or all of days 5-12. In some regimes, one dose is administered within days 1-4 and other dose within days 5-12. Doses can be e.g., 1-3 mg/kg preferably 2-3 mg/kg or 2.6 mg/kg.

The PSD-95 inhibitor can be administered in the form of a pharmaceutical composition. Pharmaceutical compositions are typically manufactured under GMP conditions. Pharmaceutical compositions for parenteral administration are preferentially sterile (e.g., filter sterilization of peptide) and free of pyrogens. Pharmaceutical compositions can be provided in unit dosage form (i.e., the dosage for a single administration). Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

An exemplary formulation of the chimeric agent Tat-NR2B9c contains the peptide in normal saline (0.8-1.0% and preferably 0.9% saline) or phosphate buffered saline at a concentration of 10-30 mg/ml, for example 16-20 or 18 mg/ml. When stored frozen, such a composition is stable (insignificant degradation or aggregation of the peptide) for a period of two or more years. Although additional excipients can be added, normal saline or phosphate buffered saline without such excipients is sufficient to obtain this stability. For use such a composition is thawed and diluted into a larger volume of normal saline for infusion into a blood vessel.

Many examples of pharmacological agent for reperfusion are in clinical use. Such agents can be used in the present combination methods in accordance with their conventional formulations, doses, routes of administration, and frequency of administration (see Physician's Desk Reference and applicable package inserts). Likewise, mechanical methods of reperfusion can be employed in accordance with conventional practice.

EXAMPLES

Example 1

Neuroprotection by Tat-NR2B9C after Ischemic Stroke or Brain Hemorrhage

Study Design

We conducted a randomized, double blind, placebo-controlled trial in which patients were enrolled from September 2008 through March 2011 at 14 hospitals in Canada and the USA. The trial was approved by local and national institutional review boards, and informed consent was obtained from the patients or from legally acceptable surrogates. The inclusion and exclusion criteria are summarized in Table 4. All patients received treatment of their aneurysm and, in the case of a ruptured aneurysm, of their subarachnoid haemorrhage, in accordance with local institutional treatment practices.

TABLE 4

Major Inclusion and Exclusion Criteria

Inclusion Criteria

Ruptured or unruptured brain aneurysm deemed suitable for repair by neuroendovascular techniques involving detachable platinum coils, stent-assisted coiling, flow-diverting stents, balloon-assisted coiling, covered stents, neck-bridge devices, or any other adjunctive devices
Recoiling or re-treatment of previously treated aneurysm
If ruptured aneurysm Endovascular repair must take place within 72 hours of the ictal haemorrhage
Subject should be WFNS Grade I-III
Body weight less than or equal to 180 kg
Normal or abnormal but not clinically significant findings in the non-neurological physical exam, 12-lead ECG and vital signs
Absence of ongoing ischemic symptoms such as TIAs, minor strokes, stroke-in-evolution, or clinical evidence of cerebral vasospasm within 2 weeks prior to randomization
Brain MRI within 2 weeks prior to the endovascular repair
Male or female with a minimum age of 18 years
Females of childbearing potential must have a negative pregnancy test and be willing to use birth control for 3 months after completion of dosing
Non-surgically sterile males or males with partners of childbearing potential must be willing to use condoms with spermicide for 3 months
Signed informed consent and availability of the subject for the entire study period Exclusion Criteria Dissecting or mycotic brain aneurysm
Planned endovascular vessel sacrifice as the primary modality for aneurysm treatment
Known history of life-threatening allergic reaction to any medication
Chronic renal disease defined as a baseline serum creatinine >150 μmol/L
Women who are breastfeeding
Any clinically significant psychiatric or psychological disease which would preclude subject from completing protocol
Pre-morbid (estimated) modified Rankin scale score of >2
Previous serious traumatic brain injury that would preclude the subject from completing the protocol or preclude MRI analysis of small strokes
Subjects who are unable to have an MRI scan for any reason
Participation in another clinical trial with an investigational drug within 30 days of this study including ENACT or prior receipt of TAT-NR2B9C
Any other medical condition that would put the subject at excessive risk of participation in the study, or an expected life expectancy <1 year or that would result in inability to collect clinical outcomes at Day 30

Clinical and MRI Assessments

All clinical and MRI assessments were performed by individuals who were unaware of the treatment assignment. Each enrolled patient underwent an MRI scan on a (minimum) 1.5T scanner within 2 weeks prior to the endovascular procedure and at 24-96 hours thereafter. Each scan included the following minimum sequences: an axial FLAIR: 3 mm, no gap, an axial DWI: 3 mm, no gap and an axial 3D T1 weighted gradient echo sequence 2.0 mm (e.g. FSPGR on GE machine).

Patients were assessed at the time of enrolment, post-procedure, and over a 30 day study period as detailed in Table 5. Initial assessments included a physical examination, neuroimaging, baseline scoring on the National Institutes of Health Stroke Scale (NIHSS) and the modified Rankin scale (mRS) and a neurocognitive battery (detailed in Table 6). For patients with ruptured aneurysms, baseline neurocognitive testing was omitted, the subarachnoid haemorrhage (SAH) was assigned a Fisher grade and its clinical severity was scored according to the World Federation of Neurosurgical Societies (WFNS) grading system. The NIHSS is a 15-item scale that measures the level of neurologic impairment. Scores range from 0 to 42, with a higher score indicating greater stroke severity. The mRS is a measure of disability that ranges from 0 (no symptoms at all) to 6 (death); a score of 5 indicates severe disability (the patient is bedridden and incontinent and requires constant nursing care and attention). The WFNS system (Grades 1-5) rates the clinical condition of a SAH patient according to the Glasgow Coma Score (GCS), where Grade 1 is normal, and Grade 5 is GCS <7. The Fisher grading system classifies the appearance of subarachnoid hemorrhage on a CT in order to predict the risk of cerebral vasospasm. The examiners were trained and certified in the use of all scales. Clinical assessments post-procedure and drug infusion were focused primarily on cardiorespiratory safety, neurological function, and neurocognition. For patients with ruptured aneurysms, neurocognitive studies were only performed on day 30.

TABLE 5

Clinical, biochemical and MRI assessment flow chart.

| | Study Period | | | |
|---|---|---|---|---|
| Procedure | Enrolment (Within 14 d of Day 1) | Dosing Day 1 | Days 2-4 (24-96 hours) | End of Study (Day 30 ± 7 d) |
| Informed Consent | X | | | |
| Medical and Surgical History | X | | | |
| Demographics | X | | | |
| WFNS and Fisher Grade (ruptured aneurysm patients only) | X | | | |
| Modified Rankin Scale (mRS) | X | | X | X |
| NIH Stroke Scale (NIHSS) | X | $X^1$ | X | X |
| Cognitive Battery[2] | X | | X | X |
| Physical/Neurological Examination | X | $X^3$ | | X |
| Vital Signs Measurement[4] | $X^5$ | $X^6$ | $X^7$ | $X^7$ |
| Height | X | | | |
| Weight | X | | $X^8$ | |
| ECG | X | $X^9$ | $X^{10}$ | |
| Histamine Sample Collection[11] | | X | | |
| Bioanalytical Sample Collection[12] | | X | | |
| Biochemistry, Hematology, Urinalysis | X | $X^{13}$ | $X^{13}$ | X |
| Serum β-hCG Testing[14] | X | X | | X |
| Urine Pregnancy Testing[14] | | X | | |

TABLE 5-continued

Clinical, biochemical and MRI assessment flow chart.

| | Study Period | | | |
|---|---|---|---|---|
| Procedure | Enrolment (Within 14 d of Day 1) | Dosing Day 1 | Days 2-4 (24-96 hours) | End of Study (Day 30 ± 7 d) |
| Plasma sample for storage (for possible immunogenicity testing) | | X[15] | | X |
| MRI Imaging: DWI and FLAIR sequences | X | | X | |

[1] 1-4 hours post exit from the angiography suite
[2] Enrolment and Days 2-4 assessment omitted for patients with a ruptured aneurysm (performed on Day 30 only).
[3] Postdose.
[4] Cardiac monitoring was performed on Day 1 from 0 to 2 hours post-dose.
[5] Blood pressure, heart rate, temperature, $SaO_2$.
[6] Neurovital signs performed at least every 4 hours until 24 hours after dosing and then as determined by the treating physician(s). BP, HR, and $O_2$ saturation to were measured pre-procedure (i.e., pre-anesthesia induction) and post-procedure (immediately pre-dose). BP and HR: 0.5, 1, 2, 3, 4, 5, 6, 9, 12, 16, 20 and 24 hours post-dose. Temperature measured once 12-24 hours post-dose. $O_2$ saturation: 0.5, 1, 2, 3, 4, 5, 6 post-dose, but could be discontinued after termination of, and recovery from, anesthesia, and is was not required beyond 6 hours post-dose.
[7] Blood pressure, heart rate, temperature.
[8] Weight to be measured for all patients at Enrolment and Day 2-4. In the case of ruptured aneurysm patients whose weight has to be estimated at Enrolment (following clinical practice), actual weight is required to be measured by Day 2-4.
[9] 12-lead ECG pre-dose, 4-6 hours, and 12 hours post-dose. If Enrolment and Day 1 occur on the same day, one 12-lead ECG may be performed to serve as both the Enrolment and Day 1 pre-dose ECG. (Minimum of) 3-lead ECG monitoring will be performed by the anaesthesiologist and/or post-operative recovery room staff from onset of dosing until at least 2 hours post-dose.
[10] 12-lead ECG 24 hours post-dose
[11] Two samples taken at predose and at 10 minutes after the termination of the study drug infusion.
[12] Two consecutive samples for PK analysis, taken between 5 and 10 minutes after the start of the study drug infusion.
[13] As per institutional practice patterns in the treatment of patients with brain aneurysms post-endovascular treatment.
[14] For women of childbearing potential only; either urine or serum testing can be performed predose on Day 1. See section 8.5.2 for further details.
[15] Predose

TABLE 6

Day 30 Neurocognitive Outcomes

| Test | Direction* | Placebo Mean ± SD N= | TAT-NR2B9C Mean ± SD N= | P Value |
|---|---|---|---|---|
| | | All Randomized Subjects Day 30 | | |
| Trails A | ↓ | 48.10 ± 34.20 | 37.55 ± 18.50 | 0.083 |
| Trails B | ↓ | 115.27 ± 77.80 | 101.12 ± 75.10 | 0.402 |
| Phonemic Verbal Fluency | ↑ | 36.20 ± 13.10 | 34.80 ± 12.00 | 0.469 |
| Semantic Verbal Fluency | ↑ | 17.78 ± 5.48 | 16.36 ± 4.91 | 0.075 |
| Digit Symbol | ↑ | 65.04 ± 22.40 | 60.58 ± 21.10 | 0.186 |
| HVLT-R Total Recall | ↑ | 23.22 ± 5.24 | 22.70 ± 6.26 | 0.555 |
| HVLT-R Delayed Recall | ↑ | 8.09 ± 2.59 | 7.37 ± 3.25 | 0.109 |
| HVLT-R Retention % | ↑ | 85.10 ± 18.70 | 76.61 ± 26.90 | 0.017 |
| HVLT-R RDI | ↑ | 10.02 ± 1.69 | 9.63 ± 2.61 | 0.240 |
| MMSE | ↑ | 28.50 ± 1.68 | 28.50 ± 2.62 | 1.000 |
| NPI-Q Severity Score | ↓ | 3.48 ± 4.73 | 1.80 ± 2.32 | 0.014 |
| NPI-Q Distress Score | ↓ | 3.23 ± 5.23 | 1.56 ± 2.49 | 0.026 |
| CES-D | ↓ | 11.62 ± 11.20 | 10.75 ± 8.11 | 0.556 |
| | | Unruptured Subjects Day 30 | | |
| Trails A | ↓ | 46.22 ± 32.80 | 36.03 ± 19.10 | 0.115 |
| Trails B | ↓ | 107.86 ± 72.36 | 96.601 ± 73.48 | 0.517 |
| Phonemic Verbal Fluency | ↑ | 37.67 ± 12.00 | 34.68 ± 12.40 | 0.146 |
| Semantic Verbal Fluency | ↑ | 18.32 ± 4.58 | 16.13 ± 4.72 | 0.006 |
| Digit Symbol | ↑ | 66.88 ± 21.70 | 62.12 ± 21.10 | 0.196 |
| HVLT-R Total Recall | ↑ | 23.70 ± 4.96 | 23.12 ± 6.00 | 0.528 |
| HVLT-R Delayed Recall | ↑ | 8.33 ± 2.54 | 7.43 ± 3.15 | 0.063 |
| HVLT-R Retention % | ↑ | 86.71 ± 18.20 | 76.17 ± 25.7 | 0.005 |
| HVLT-R RDI | ↑ | 10.01 ± 1.75 | 9.68 ± 2.64 | 0.370 |
| MMSE | ↑ | 28.50 ± 1.73 | 28.71 ± 2.33 | 0.661 |
| NPI-Q Severity Score | ↓ | 2.95 ± 4.19 | 1.57 ± 2.02 | 0.046 |
| NPI-Q Distress Score | ↓ | 2.62 ± 4.39 | 1.31 ± 2.07 | 0.068 |
| CES-D | ↓ | 11.35 ± 11.00 | 9.57 ± 7.81 | 0.272 |
| | | Ruptured Subjects Day 30 | | |
| Trails A | ↓ | 61.60 ± 45.50 | 45.14 ± 13.70 | 0.3807 |
| Trails B | ↓ | 168.60 ± 103.00 | 123.71 ± 85.10 | 0.4272 |
| Phonemic Verbal Fluency | ↑ | 27.92 ± 16.30 | 35.29 ± 10.90 | 0.1498 |

TABLE 6-continued

Day 30 Neurocognitive Outcomes

| Test | Direction* | Placebo Mean ± SD N= | TAT-NR2B9C Mean ± SD N= | P Value |
|---|---|---|---|---|
| Semantic Verbal Fluency | ↑ | 14.77 ± 8.68 | 17.22 ± 5.63 | 0.3473 |
| Digit Symbol | ↑ | 54.85 ± 24.10 | 54.94 ± 20.70 | 0.9904 |
| HVLT-R Total Recall | ↑ | 20.54 ± 6.13 | 21.11 ± 7.13 | 0.8169 |
| HVLT-R Delayed Recall | ↑ | 6.77 ± 2.55 | 7.17 ± 3.67 | 0.7395 |
| HVLT-R Retention % | ↑ | 76.05 ± 19.5 | 78.25 ± 31.9 | 0.8269 |
| HVLT-R RDI | ↑ | 10.08 ± 1.32 | 9.44 ± 2.55 | 0.4209 |
| MMSE | ↑ | 28.50 ± 1.29 | 27.43 ± 3.78 | 0.6033 |
| NPI-Q Severity Score | ↓ | 5.08 ± 5.99 | 2.53 ± 3.07 | 0.161 |
| NPI-Q Distress Score | ↓ | 5.08 ± 7.09 | 2.40 ± 3.50 | 0.2069 |
| CES-D | ↓ | 13.15 ± 12.2 | 15.28 ± 7.80 | 0.5591 |

*↑ The higher the score the better the test performance
↓ The lower the score the better the test performance Study Interventions Patients were randomly assigned by a computer-generated coding system to receive an intravenous infusion of either TAT-NR2B9C or Placebo. The study drug was supplied as a drug vial containing 20 mg/ml TAT-NR2B9C, which was dosed at 2.6 mg/kg by dilution in 100 cc normal saline and infused intravenously over 10 minutes. Infusion, performed by individuals blinded to the treatment assignment, began once the treating neurointerventionalist deemed the aneurysm repair to be completed but prior to termination of anesthesia. The rationale for this timing was that the purpose of ENACT was to test whether neuroprotection in humans is feasible after a stroke has occurred, and not just in a pre-treatment paradigm.

Assessment of Stroke Number and Volume

New ischemic lesions were defined as new hyperintense signals on the day 2-4 DWI MRI (FIGS. 1A-C; yellow arrows; termed DWI lesions). The volume of new DWI lesions was determined from the surface area of regions of interest (ROIs) traced around each DWI lesion (FIGS. 1A-C), multiplied by the slice thickness (3 mm). Lesions on FLAIR imaging were deemed to be new if they fell within the location of a new DWI lesion and did not pre-exist on the enrolment MRI (FIGS. 1A-C). The volumes of new FLAIR lesions were determined similarly to that of new DWI lesions. All calculations were performed using Osirix software (v.3.9.2, 32 bit version).

Outcome Measures

The main purpose of ENACT was to test the neuroprotection hypothesis, Thus the effect of TAT-NR2B9C on the number and volume of detectable new lesions was of primary interest. However, the ENACT paradigm has never been previously conducted, and the MRI assessments provided 4 measures of equal interest (DWI lesion number, DWI lesion volume, FLAIR lesion number and FLAIR lesion volume). We selected as the primary efficacy outcome measure the ability of a single intravenous dose of TAT-NR2B9C to reduce the volume of embolic strokes as measured by DWI and FLAIR MRI Imaging at 24-96 hours post-procedure. Another objective of primary interest was to determine the safety and tolerability of TAT-NR2B9C in the present patient population. Secondary outcomes included the efficacy of TAT-NR2B9C in reducing the number of embolic strokes, efficacy in patients sustaining small strokes (<10 cc's), in reducing procedurally-induced cognitive impairment at the day 30 follow-up, in reducing the frequency of large (>10 cc strokes), and in improving outcome (new strokes, neurological and neurocognitive) in the subgroups of patients with ruptured and unruptured aneurysms.

Statistical Analysis

Data were analyzed according to the modified intent-to-treat (mITT) principle; ITT; and per protocol populations. Under the mITT principle, the evaluable sample includes all subjects who are randomized and receive any amount of study drug. In the case of missing data on clinical outcome among patients known to be alive, the worst possible outcome score was assigned. P values are presented unadjusted and, where indicated, adjusted for variables that impact the outcome measure.

Results

Study Patients

Figure 2:
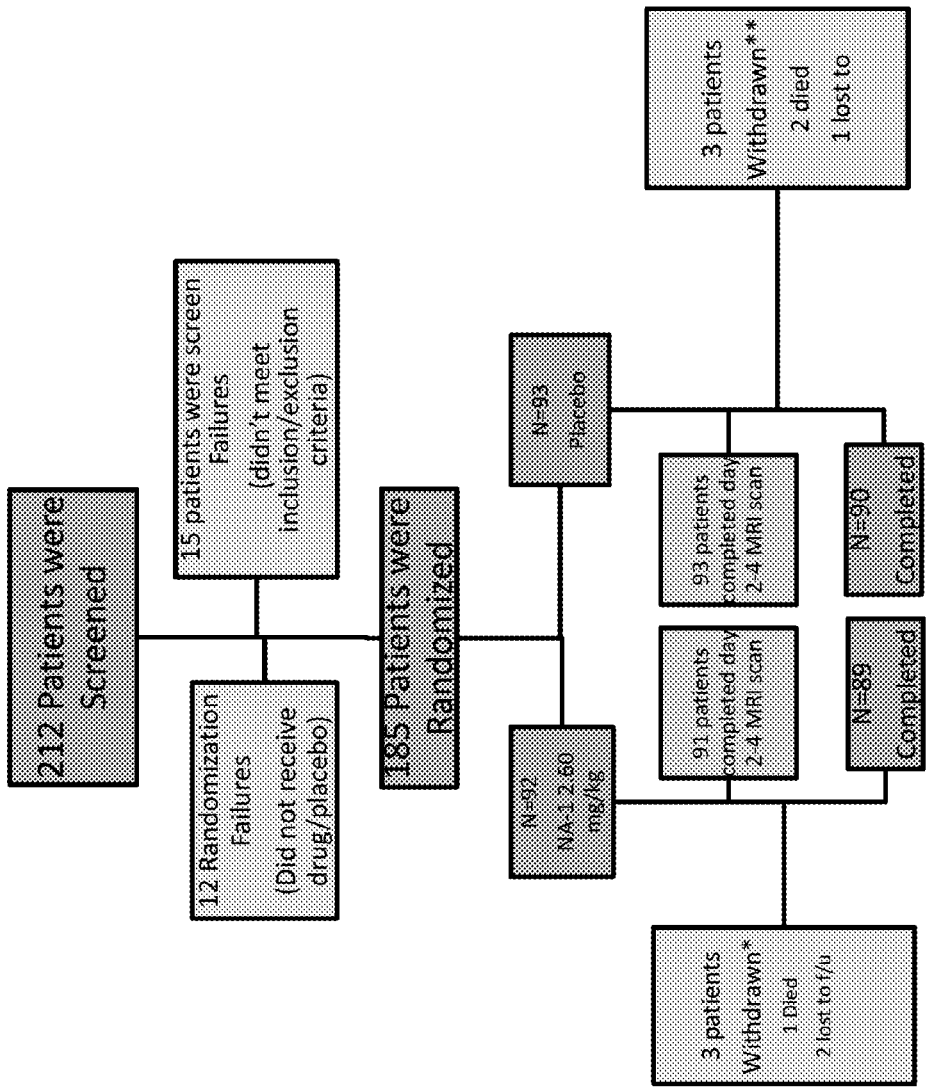
FIG. 2. Numbers of patients who were screened, randomly assigned to a study group, and included in the per-protocol population. The modified intention-to-treat population was defined as all patients who were enrolled and randomly assigned to a study group and who received study drug (TAT-NR2B9C or Placebo). The per-protocol population was defined as all randomly assigned patients who received TAT-NR2B9C or placebo and who were not excluded because of major protocol violations, which included the inability to complete the post-endovascular procedure MRI scans (1 patient, who died before a scan could be done), or lack of attendance at the 30 day end-of-study visit due to death or refusal to return for follow-up. However, of the 185 patients who were randomized, 184 completed their day 2-4 post-procedure MRI scans, and these were included in the analysis.

The disposition of all study patients is provided in FIG. 2. Between September, 2008, and March 2011, 212 patients from 11 Canadian and 3 USA sites were screened in accordance with the inclusion/exclusion criteria of the Trial (Table 4). 15 did not meet the criteria and were not randomized. There were 12 randomization failures (Patient randomized, but did not receive study drug): 5 due to inability to carry out the endovascular aneurysm repair, 3 due to inability to obtain a pre-procedure MRI (planned on the same day as the procedure), 2 due to a pre-procedure ECG showing a QTc interval >450 ms (an exclusion criterion), 1 due to a fatal aneurysm rupture during the procedure and prior to drug infusion and 1 due to refusal by the anesthesiologist to administer study drug in a patient with severe chronic obstructive pulmonary disease. A total of 185 patients were thus randomized and received study drug (the mITT population), such that 92 patients were randomly assigned to receive TAT-NR2B9C and 93 patients were assigned to receive placebo (FIG. 2). In the TAT-NR2B9C group, 1 patient died prior to the day 2-4 MRI scan and 2 refused to attend their day 30 follow up. In the placebo group, 2 subjects died after the day 2-4 MRI scan, and a third did not attend the day 30 follow up (FIG. 2).

Baseline demographic and clinical characteristics of the two groups were similar (Table 7). The endovascular procedures lasted, on average, about 2 hours (Table 7). About half of the aneurysm repairs could be performed using only detachable platinum coils, whereas in the rest, additional assistive techniques or devices were used comprising of balloon or stent-assisted coiling or repair using flow-diverting stents. There were no differences in the baseline and clinical characteristics between the TAT-NR2B9C and Placebo groups in the subgroups of patients with ruptured or unruptured aneurysms, except for a higher incidence of hypertension in patients with ruptured aneurysms treated with placebo (Table 7).

TABLE 7

Demographic and Baseline Characteristics of the Patients

| | All Randomized Study Group | | | Unuptured Aneurysm Study Group | | | Ruptured Aneurysm Study Group | | |
|---|---|---|---|---|---|---|---|---|---|
| Characteristic | Placebo (N = 93) | NA-1 (N = 92) | P * | Placebo (N = 74) | NA-1 (N = 74) | P * | Placebo (N = 19) | NA-1 (N = 18) | P * |
| Age (yr) | 56.05 ± 10.3 | 58 ± 11.05 | 0.21 | 56.48 ± 19.7 | 58.78 ± 9.7 | 0.17 | 54.47 ± 9.12 | 55.0 ± 15.44 | 0.90 |
| Male sex (%) | 26.90% | 30.40% | 0.63 | 20.73% | 31.08% | 1.00 | 15.79% | 27.78% | 0.45 |
| Weight (Kg) | 76.4 ± 16.5 | 75.0 ± 20.1 | 0.62 | 77.4 ± 17.2 | 75.6 ± 20.0 | 0.55 | 72.6 ± 13.1 | 72.8 ± 25.2 | 0.97 |
| Syst. pressure (mm Hg) | 130.5 ± 14.4 | 130.2 ± 16.2 | 0.87 | 130.9 ± 14.1 | 7 | 0.95 | 129 ± 16.1 | 126 ± 14.2 | 0.61 |
| Dias. Pressure (mm Hg) | 76.0 ± 10.0 | 75.8 ± 12.1 | 0.91 | 76.6 ± 9.00 | 77.9 ± 11.2 | 0.46 | 73.6 ± 13.1 | 67.3 ± 12.2 | 0.15 |
| Diabetes (%) | 6.50% | 5.40% | 0.77 | 6.76% | 5.41% | 1.00 | 5.26% | 5.56% | 1.00 |
| Hypertension (%) | 50.50% | 42.40% | 0.8 | 45.95% | 45.95% | 1.00 | 68.43% | 27.78% | 0.02 |
| Hyperlipidemia (%) | 10.80% | 11.00% | 0.8 | 9.46% | 12.16% | 0.79 | 15.79% | 11.11% | 1.00 |
| Smoking status (%) | | | 0.06 | | | 0.19 | | | 0.19 |
| No | 36.60% | 26.10% | | 33.78% | 25.68% | | 47.37% | 27.78% | |
| Past | 26.90% | 43.50% | | 32.43% | 47.30% | | 5.26% | 27.78% | |
| Current | 36.60% | 30.40% | | 31/78% | 27.03% | | 47.37% | 44.44% | |
| NIHSS score† | | | | | | | | | |
| Mean | 0.45 ± 2.15 | 0.22 ± 0.53 | 0.31 | 0.18 ± 0.65 | 0.19 ± 0.51 | 0.89 | 1.93 ± 5.09 | 0.35 ± 0.61 | 0.21 |
| Median | 0 | 0 | 0.22 | 0 | 0 | 0.85 | 0 | 0 | 0.11 |
| mRS | | | | | | | | | |
| Mean | 0.28 ± 0.71 | 0.17 ± 0.41 | 0.22 | 0.24 ± 0.64 | 0.16 ± 0.41 | 0.36 | 0.42 ± 0.96 | 0.22 ± 0.43 | 0.43 |
| Median | 0 | 0 | 0.16 | 0 | 0 | 0.12 | 0 | 0 | 1.00 |
| Ruptured Aneurysm (N) | 20.40% | 19.60% | 0.88 | | | | | | |
| Procedure duration (h) | 2.07 | 2.06 | 0.9 | 2.01 ± 1.10 | 2.03 ± 0.82 | 0.91 | 2.29 ± 1.00 | 2.13 ± 0.57 | 0.56 |
| Assistive device (%) | 52% | 54% | 0.71 | 50.00% | 59.46% | 0.32 | 57.89% | 33.33% | 0.19 |
| balloon | 25% | 29% | | | | | | | |
| stent | 19% | 18% | | | | | | | |
| pipeline stent | 8% | 7% | | | | | | | |
| Concom. Antiplatelet | 41.00% | 35.00% | 0.42 | 33.78% | 48.55% | 0.10 | 42.11% | 11.11% | 0.06 |

* P values were obtained using a t-test or a Fisher's exact test.
* Scores on the National Institutes of Health Stroke Scale (NIHSS) range from 0 to 42, with higher values reflecting more severe neurologic impairment (<5, mild impairment; ≥25, very severe impairment).

MRI Outcomes

Of 185 randomized subjects, 184 completed the post-procedure (day 2-4) MRI scan. Patients who were treated with TAT-NR2B9C after their endovascular procedure exhibited a 43% reduction in the number of new ischemic lesions as detected by DWI MRI (Table 8; p=0.005). This was also reflected in the FLAIR MRI scans, in which treatment with TAT-NR2B9C reduced the number of new ischemic lesions by 39% (Table 8; p=0.026). The median stroke volumes as measured by FLAIR and DWI MRI were also reduced in patients treated with TAT-NR2B9C (Table 8; p<0.001 for both DWI and FLAIR volumes [using a Rank-Ordered Logistic Regression in Stata]). However, due to the skewed and widely dispersed distribution of the volumes data (Table 8), mean infarct volumes were significantly distorted by patients who exhibited large strokes (defined as >10 cc's). Specifically, two patients assigned to the TAT-NR2B9C group suffered from complications during the aneurysm repair procedure that caused large strokes (10.7 cc and 49.2 cc). This produced non-significant overall differences in mean stroke volumes between the treatment groups.

TABLE 8

MRI Outcomes

| | | All Patients | | | | |
|---|---|---|---|---|---|---|
| | | Study Group | | | | |
| | | Placebo | | TAT-NR2B9C | | P Value | |
| | | (N = 93) | | (N = 91) | | P Value | P Value |
| MRI Parameter | | Mean | Median | Mean | Median | Unadj* | Adj** |
| Number of DWI Lesions | | 7.28 ± 12.61 | 2 | 4.13 ± 6.81 | 2 | 0.018 | 0.005 |
| Number of FLAIR Lesions | | 4.83 ± 7.69 | 2 | 2.96 ± 4.42 | 1 | 0.048 | 0.026 |
| Volume of DWI Lesions (mm3) | | 645 ± 1382 | 123.9 | 966 ± 5266 | 59.4 | 0.306 | 0.120 |
| Volume of FLAIR Lesions (mm3) | | 477 ± 1611 | 44.9 | 915 ± 5598 | 29.1 | 0.445 | 0.236 |

TABLE 8-continued

MRI Outcomes

| | Patients with Ruptured Aneurysms | | | | | |
|---|---|---|---|---|---|---|
| | Placebo (N = 19) | | TAT-NR2B9C (N = 18) | | P Value | P Value |
| | Mean | Median | Mean | Median | Unadj* | Adj** |
| Number of DWI Lesions | 9.47 ± 11.59 | 4 | 3.39 ± 5.93 | 1 | 0.027 | |
| Number of FLAIR Lesions | 6.58 ± 7.48 | 4 | 2.39 ± 4.67 | 0 | 0.046 | |
| Volume of DWI Lesions | 1373 ± 2267 | 164.6 | 277 ± 528 | 28.7 | 0.015 | |
| Volume of FLAIR Lesions | 1575 ± 3229 | 86.8 | 205 ± 495 | 0 | 0.023 | |
| | Patients with Unruptured Aneurysms | | | | | |
| | Placebo (N = 74) | | TAT-NR2B9C (N = 73) | | P Value | P Value |
| | Mean | Median | Mean | Median | Unadj* | Adj** |
| Number of DWI Lesions | 6.72 ± 12.88 | 2 | 4.32 ± 7.03 | 2 | 0.108 | 0.019 |
| Number of FLAIR Lesions | 4.38 ± 7.64 | 2 | 3.10 ± 4.39 | 1 | 0.220 | 0.084 |
| Volume of DWI Lesions | 459 ± 983 | 109.1 | 1137 ± 5870 | 72.2 | 0.933 | 0.471 |
| Volume of FLAIR Lesions | 195 ± 553 | 41.4 | 1083 ± 6215 | 33.2 | 0.617 | 0.896 |
| | Patients with Strokes <10 cc's† | | | | | |
| | Placebo (N = 93) | | TAT-NR2B9C (N = 89) | | P Value | P Value |
| | Mean | Median | Mean | Median | Unadj* | Adj** |
| Number of DWI Lesions | 7.28 ± 12.61 | 2 | 3.91 ± 6.72 | 1 | 0.010 | 0.002 |
| Number of FLAIR Lesions | 4.83 ± 7.69 | 2 | 2.75 ± 4.25 | 1 | 0.024 | 0.012 |
| Volume of DWI Lesions | 645 ± 1382 | 123.9 | 315 ± 646 | 51.5 | 0.054 | 0.009 |
| Volume of FLAIR Lesions | 477 ± 1611 | 44.9 | 183 ± 506 | 25.2 | 0.061 | 0.014 |
| | Patients w Strokes <10 cc and unrupt. aneurysms | | | | | |
| | Placebo (N = 74) | | TAT-NR2B9C (N = 71) | | P Value | P Value |
| | Mean | Median | Mean | Median | Unadj* | Adj** |
| Number of DWI Lesions | 6.72 ± 12.88 | 2 | 4.04 ± 6.94 | 2 | 0.069 | 0.010 |
| Number of FLAIR Lesions | 4.38 ± 7.64 | 2 | 2.84 ± 4.17 | 1 | 0.131 | 0.045 |
| Volume of DWI Lesions | 459 ± 983 | 109.1 | 325 ± 675 | 70.4 | 0.441 | 0.088 |
| Volume of FLAIR Lesions | 195 ± 553 | 41.4 | 178 ± 511 | 30.2 | 0.581 | 0.183 |

Plus-minus values are means ± SD;
*P values reflect a test of the differences between the means.
**Adjusted P values represent the effect of treatment, adjusted for the variables Age, Aneurysm Rupture, the use of Adjunctive Devices, procedure duration and the use of Antiplatelet Agents (ASA or Plavix).;
†As defined by DWI volume;
‡ Adjusted values not calculated due to small numbers of patients Among the patients randomized in ENACT, 37 presented with a SAH due to a ruptured aneurysm. This subgroup was preselected for a subgroup analysis due to the possibility that the SAH might impact on the likelihood of suffering new ischemic lesions. Additionally, such patients might suffer more severe neurological and neurocognitive deficits due to the SAH than patients who undergo elective procedures for unruptured aneurysms. In this patient subgroup, treatment with TAT-NR2B9C reduced the number of new ischemic lesions detected by either DWI MRI or FLAIR MRI by 64% (p=0.027 and p=0.046 for DWI and FLAIR, respectively; Table 8). Moreover, the patients treated with TAT-NR2B9C exhibited an 80% reduction in new infarct volumes as defined by DWI MRI (p=0.015), and an 87% reduction of new infarct volumes as defined by FLAIR MRI (p=0.023). In the subgroup of patients with unruptured aneurysms (n=147), the effect of treatment with TAT-NR2B9C on the MRI outcomes trended in the same directions as the overall patient cohort (Table 8).

An additional subgroup analysis was performed on patients without large strokes (182 of the 184 patients). The rationale for this analysis was that the ENACT paradigm was designed to examine the effect of treatment on small embolic strokes, similar to those modelled in the non-human primate experiments where in new ischemic lesions were consistently small. However, in such a paradigm, the arithmetic means of the infarct volumes became subject to distortion by infarcts that far exceed the median volumes observed. In patients with strokes under 10 cc's by volume, treatment with TAT-NR2B9C reduced the numbers and volumes of new ischemic lesions as detected by DWI and by FLAIR MRI (Table 8), consistent with a neuroprotective effect of TAT-NR2B9C in small, procedurally-induced strokes. Thus, the MRI methods described herein can also be useful for screening the effects of other neuroprotective drugs in ischemic stroke, hemorrhagic stroke, and SAH.

A secondary objective in ENACT was to determine whether TAT-NR2B9C treatment reduces the frequency of large (>10 cc) strokes. However, the 2 occurrences of large strokes were insufficient to warrant statistical analysis.

Neurological Outcomes

Patients enrolled in ENACT either underwent elective aneurysm repair or experienced a SAH with WFNS scores of I-III (Glascow Coma Score 13-15). Consequently, they exhibited a low level of neurological disability at the time of the endovascular procedure (median NIHSS and mRS of 0; Table 7). On day 30 Post-procedure, 93.5% of all patients who were treated with TAT-NR2B9C and 89.2% of patients treated with Placebo had favourable NIHSS scores (NIHSS 0-1, p=0.434; Table 9). mRS scores were favorable (0-2) in 93.5% in each of the TAT-NR2B9C and placebo groups (Table 9). However, in subjects enrolled with ruptured aneurysms, 100% of those treated with TAT-NR2B9C had favorable NIHSS 30 days post-procedure, as compared with 68.4% of patients treated with placebo (p=0.020; Table 4). SAH patients treated with TAT-NR2B9C also trended to having more favorable mRS scores as compared with those treated with placebo (94.4% vs 73.7% in TAT-NR2B9C and placebo, respectively; p=0.180; Table 9). The patients who sustained large strokes (>10 cc) due to procedural complications were in the TAT-NR2B9C group. On day 30, one had a NIHSS of 2 and mRS of 2, and the other an NIHSS of 2 and mRS of 1.

TABLE 9

Neurological Outcomes

| | Study Group | | |
|---|---|---|---|
| | Placebo no**. (%) | TAT-NR2B9C | P value |
| All Patients | (N = 93) | (N = 92) | |
| NIHSS of 0 or 1 | 83 (89.2%) | 86 (93.5%) | 0.434 |
| mRS score of 0-2 | 87 (93.5%) | 86 (93.5%) | 1.000 |
| Patients with Unruptured Aneurysms | (N = 74) | (N = 74) | |
| NIHSS of 0 or 1 | 70 (94.6%) | 68 (91.9%) | 0.745 |
| mRS score of 0-2 | 73 (98.6%) | 69 (93.2%) | 0.363 |
| Patients with Ruptured Aneurysms | (N = 19) | (N = 18) | |
| NIHSS of 0 or 1 | 13 (68.4%) | 18 (100%) | 0.020 |
| mRS score of 0-2 | 14 (73.7%) | 17 (94.4%) | 0.180 |
| Patients with strokes < 10 cc's** | (N = 93) | (N = 89) | |
| NIHSS of 0 or 1 | 83 (89.3%) | 85 (95.5%) | 0.164 |
| mRS score of 0-2 | 87 (93.6%) | 84 (96.6%) | 0.499 |
| Unruptured Aneurysm Patients with strokes < 10 cc's** | (N = 74) | (N = 71) | |
| NIHSS of 0 or 1 | 70 (94.6%) | 67 (94.4%) | 1.000 |
| mRS score of 0-2 | 73 (98.7%) | 67 (97.1%) | 0.609 |

Neurocognitive Outcomes

Outcomes from the battery of neurocognitive tests are detailed in Supplementary Table 7. TAT-NR2B9C treated patients showed neurocognitive benefits after treatment with TAT-NR2B9C, including significant improvements in the neuropsychiatric inventory questionnaires. Surprisingly, although the numbers of patients were small for statistical analysis in the ruptured aneurysm group, there were significant trends of improvement in cognitive and neuropsychiatric tests for patients treated with TAT-NR2B9C.

Safety

A total of 3 patients died. One, enrolled with an unruptured aneurysm, had received TAT-NR2B9C but died on day 3 due to hemorrhagic shock from a retroperitoneal hematoma induced by the groin puncture. Two received placebo. One died on day 13 from neurological complications following an intra-procedural rupture of a previously unruptured aneurysm. The other, enrolled with a ruptured aneurysm, died on day 12 due to neurological complications of the SAH.

A listing of Adverse Events (AEs), including Severe and Serious AE's, is provided in Table 5. Overall, the AE's were well balanced between the treatment groups. There were a total of 388 AEs in Placebo, and 336 AEs in the TAT-NR2B9C group. However, only 2 AEs were deemed to be probably related to drug and both were mild-consisting of transient hypotension that resolved within minutes. Of all Serious AEs (AEs that result in death, are life-threatening, require a new hospitalization or prolong current hospitalization, or result in a persistent or significant disability or incapacity), 24 occurred in 14 patients who received placebo, and 11 occurred in 9 patients who received TAT-NR2B9C (Table 10). None were related to TAT-NR2B9C.

Another surprising finding is that patients receiving TAT-NR2B9C had significantly fewer incidents of pain reported associated with the procedure. Although the number of patients reporting pain associated with the aneurysm repair procedures was not high,ced the effect was large enough that there is a P value of less than <0.02. Thus, TAT-NR2B9C can reduce procedural and post-procedural pain in humans, and is likely to reduce pain either without aneurysm repair procedures or in other procedures that have pain associated with them as a side effect. As PSD-95 and the NMDAR2 subunits are also highly conserved in animals, PSD-95 inhibitors are likely to be effective in animals for pain as well.

TABLE 10

Safety End Points and Adverse Events (AEs).

| | Study Group | | | |
|---|---|---|---|---|
| | Placebo (N = 93) | TAT-NR2B9C (N = 92) | Odds Ratio | P Value |
| Most Common Adverse Events (>10% in any Treatment Group) | | | | |
| Total Subjects With 1 + AE | 85 (91%) | 83 (90%) | | |
| Headache | 37 (40%) | 42 (46%) | | 0.4199 |
| Nausea | 27 (29%) | 33 (36%) | | 0.3206 |
| Vomiting | 8 (9%) | 12 (13%) | | 0.3307 |
| Procedural Pain | 10 (11%) | 2 (2%) | | 0.0178 |
| Hypotension | 6 (6%) | 9 (10%) | | 0.4066 |
| Hypertension | 7 (8%) | 4 (4%) | | 0.3606 |
| AE relationship to Study Drug | | | | |
| Total: | 388 (100%) | 336 (100%) | | |
| Unrelated | 271 (37.4%) | 251 (34.7%) | | |
| Unlikely related | 96 (13.3%) | 72 (9.9%) | | |
| Possibly related | 21 (2.9%) | 11 (1.5%) | | |
| Probably related | 0 (0.0%) | 2 (0.3%) | | |
| Total Adverse Events | | | | |
| Mild | 208 (28.7%) | 187 (25.8%) | | |
| Moderate | 159 (22.0%) | 121 (16.7%) | | |
| Severe* | 21 (2.9%) | 28 (3.9%) | | |
| Serious** Adverse Events by Body System | | | | |
| Total | 24 (14) | 11 (9) | | |
| Gastrointestinal | 2 (2) | 0 (0) | | |
| Administration Site | 0 (0) | 1 (1) | | |
| Procedural Complications | 2 (2) | 1 (1) | | |
| Nervous System | 14 (9) | 3 (3) | | |
| Genitourinary | 1 (1) | 1 (1) | | |
| Respiratory | 2 (1) | 2 (1) | | |
| Vascular | 3 (3) | 3 (3) | | |
| Infectious | 0 (0) | 0 (0) | | |
| Neoplastic | 0 (0) | 0 (0) | | |
| Blood and Lymphatic | 0 (0) | 0 (0) | | |
| immune | 0 (0) | 0 (0) | | |

TABLE 10-continued

Safety End Points and Adverse Events (AEs).

| | Study Group | | | |
|---|---|---|---|---|
| | Placebo (N = 93) | TAT-NR2B9C (N = 92) | Odds Ratio | P Value |
| Endocrine | 0 (0) | 0 (0) | | |
| Metabolic and nutritional | 0 (0) | 0 (0) | | |
| Psychiatric | 0 (0) | 0 (0) | | |
| Eye | 0 (0) | 0 (0) | | |
| Ear/Labyrinth | 0 (0) | 0 (0) | | |
| Cardiac | 0 (0) | 0 (0) | | |
| Hepatobiliary | 0 (0) | 0 (0) | | |
| Skin | 0 (0) | 0 (0) | | |
| Muskuloskeletal | 0 (0) | 0 (0) | | |
| Renal | 0 (0) | 0 (0) | | |
| congenital/familial/ genetic | 0 (0) | 0 (0) | | |

*Severe AE is defined as an incapacitating adverse events that precludes the performance of normal activities
**Serious AE is defined as an AE that results in death, is life-threatening, requires a new hospitalization or prolongs current hospitalization, results in a persistent or significant disability or incapacity, or is a congenital or birth defect.

Discussion

This trial of TAT-NR2B9C in procedurally induced strokes showed benefit of TAT-NR2B9C in reducing the numbers and the median volumes of embolic strokes in patients with ruptured and unruptured intracranial aneurysms. In the pre-specified subgroup analyses, the patients who benefited the most were those who were enrolled with a SAH due to a ruptured aneurysm, where treatment with TAT-NR2B9C reduced the numbers of strokes by 64% and the volumes by about 80%. Additionally, this subgroup of patients exhibited improved neurological outcomes by NIHSS, and trended to improved neurological outcomes by mRS and improved cognitive outcomes. Despite the small size of this subgroup of subjects with ruptured aneurysms (37 patients), the size of the TAT-NR2B9C effect was so large so as to produce statistically significant results. This is surprising given that the benefit of TAT-NR2B9C treatment is thought to occur primarily through the reduction of ischemia, and ischemia is rarely seen before day 5 in SAH.

The validity of the overall results of ENACT is supported by several features of the trial. ENACT was conducted in a double-blinded manner such that patients, investigators and those analyzing the trial results were unaware of treatment assignments. Demographic features that may influence outcomes from strokes or SAH were balanced and showed no interaction with the treatment effect.

Most subjects in ENACT (80%) had unruptured aneurysms, for which the 30d mortality and morbidity of endovascular repair, including neurological and cognitive deficits, is <10%. By contrast, those with a SAH are at greater risk of sustaining impairments in neurological and/or cognitive function. Nonetheless, the trend to improvement in the small SAH patient subgroup was surprising, as ENACT was designed to test the neuroprotection hypothesis primarily using MRI criteria, in subjects at risk of mainly small embolic strokes, and in a relatively small patient population. In patients with a SAH, neurological status on enrollment was good (median mRS and NIHSS of 0 in both placebo and TAT-NR2B9C groups). The deterioration in SAH patients untreated with TAT-NR2B9C at 30 days post treatment suggests worsening of their clinical status after their initial assessments. The worsening may result from such being more susceptible to neurological or cognitive complications of endovascular coiling, or because of SAH initiating a cascade of clinically-deleterious events. In any event, subjects with SAH receiving TAT-NR2B9C have a significantly better clinical outcome than subjects with SAH that do not.

Discussion of Cerebral Ischemia in SAH

Patients with a SAH are at risk of suffering various different complications of their SAH. These complications may independently cause injury to the brain and affect clinical outcome. Such complications include the original brain injury incurred by the sudden rise in intracranial pressure (ICP) as a result of the aneurysm rupture, as well as more delayed complications such as hydrocephalus or cerebral ischemia due to cerebral vasospasm.

Cerebral ischemia in SAH is the result of cerebral arterial vasospasm, and complicates the clinical course of approximately 30% of cases. The incidence of clinically-relevant vasospasm in SAH is highest between days 5 and 12 after the SAH. However, this complication is quite uncommon in the first three days after a SAH. A patient's ultimate clinical outcome after a SAH likely depends on the several factors, including demographic factors such as age and co-morbidities, the severity of the SAH, and the various complications of the SAH such as hydrocephalus and vasospasm. Many lines of evidence demonstrate that cerebral ischemia due to vasospasm is not the sole contributor to an adverse clinical outcome from SAH (MacDonald, 2007; Kaptain et al., 2000).

Given that TAT-NR2B9C was used in SAH subjects within 72 hours of the onset of the SAH, and given that cerebral ischemia in SAH is extremely uncommon in the first three days after SAH, the beneficial effect of TAT-NR2B9C observed in the ENACT trial in patients with a SAH is unlikely to be due to anti-ischemic effects, because TAT-NR2B9C is not being administered in a time-frame that can prevent cerebral ischemic damage in SAH. The maximum plasma concentration (Cmax) occurs within 5 minutes of the end of dose administration, and is mostly gone from the plasma in 30-45 minutes. The half-life of TAT-NR2B9C appears to be about 5 hours. Therefore TAT-NR2B9C is unlikely to still be present in a patient's central nervous system at five days, the time at which vasospasm occurrence becomes more common. Moreover, TAT-NR2B9C has been shown not to alter cerebral blood flow (Bratane et al., Stroke. 2011 November; 42(11):3265-70), and is therefore not expected to prevent vasospasm in any way.

Thus it is unlikely that TAT-NR2B9C is improving neurological outcome in SAH patients by acting on cerebral ischemia because 1) it is not vasoactive and 2) it is not administered in the time frame when cerebral ischemia is a complication of a SAH. Rather, TAT-NR2B9C may be improving neurological outcome by addressing the primary brain injury that arises after a SAH before significant cerebral ischemia has developed. Its efficacy may be due to a reduction of cell damage as a result of its disruption of cell signaling pathways that lead to the primary brain injury incurred by the rapid and transient rise in ICP that is known to arise after a SAH. Consequently, TAT-NR2B9C is addressing another factor of the various factors that may contribute to a patient's clinical outcome after a SAH, but not vasospasm or cerebral ischemia.

Although the invention has been described in detail for purposes of clarity of understanding, it will be obvious that certain modifications may be practiced within the scope of the appended claims. All publications, accession numbers, and patent documents cited in this application are hereby incorporated by reference in their entirety for all purposes to the same extent as if each were so individually denoted. To the extent more than one sequence is associated with an accession number at different times, the sequences associated with the accession number as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A method of treating a subarachnoid hemorrhage in a human subject, comprising:
administering an agent that binds to PSD-95 and inhibits binding of PSD-95 to an NMDAR2B subunit to a subject having a subarachnoid hemorrhage, wherein development of neurocognitive deficits in the subject is inhibited, wherein the administering to the subject is not in the course of a clinical trial.

2. The method of claim 1, wherein the subarachnoid hemorrhage is the result of physical trauma.

3. The method of claim 1, wherein the subarachnoid hemorrhage occurs spontaneously.

4. The method of claim 3, wherein the subarachnoid hemorrhage is due to a ruptured aneurysm.

5. The method of claim 3, wherein the subarachnoid hemorrhage is due to arteriovenous malformation.

6. The method of claim 1, wherein the agent inhibits development of infarctions detectable by MRI.

7. The method of claim 1, wherein the agent reduces pain resulting from endovascular surgery.

8. The method of claim 7, wherein the pain is along a path traversed by an endoscope used in performing the endoscopic surgery.

9. The method of claim 1, wherein the agent is administered during or after a surgery to repair a blood vessel causing the hemorrhage.

10. The method of claim 1, wherein the agent is administered before, during or after administering another agent effective to reduce damaging effects of subarachnoid hemorrhage.

11. The method of claim 1, wherein the agent is administered by day 4 following a rupture causing the subarachnoid hemorrhage.

12. The method of claim 1, wherein the agent is administered on multiple occasions within twelve days post rupture causing the subarachnoid hemorrhage.

13. The method of claim 1, wherein the agent is administered twice daily for at least two days or once daily for at least three days.

14. The method of claim 1, wherein the dose of the agent is 1-3 mg/kg.

15. The method of claim 1, wherein the agent is a peptide having an amino acid sequence consisting or comprising of $X_1tSX_2V$ (SEQ ID NO:7), wherein t and S are alternative amino acids, $X_1$ is selected from among E, Q, and A, $X_2$ is selected from among A, Q, D, N, (N-Methyl)-A, (N-methyl)-Q, (N-methyl)-D, and (N-methyl)-N, or the peptide is an agent according to a formula shown below

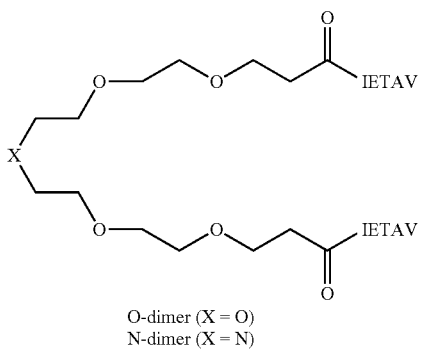

O-dimer (X = O)
N-dimer (X = N)

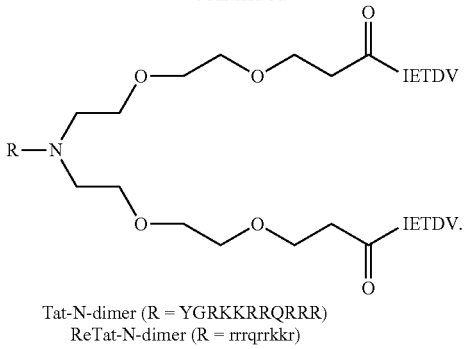

Tat-N-dimer (R = YGRKKRRQRRR)
ReTat-N-dimer (R = rrrqrrkkr)

16. The method of claim 15, wherein the peptide is linked to an internalization peptide or is lipidated thereby facilitating passage of the peptide across a cell membrane or the blood brain barrier.

17. The method of claim 1, wherein the agent is a peptide having an amino acid sequence consisting or comprising of YGRKKRRQRRRKLSSIESDV (SEQ ID NO:6) or YGRKKRRQRRRKLSSIETDV (SEQ ID NO:37).

18. The method of claim 1, wherein the agent is a myristoylated peptide.

19. The method of claim 18, wherein peptide has an amino acid sequence consisting or comprising of KLSSIESDV (SEQ ID NO:5) or KLSSIETDV (SEQ ID NO:43).

20. The method of claim 18, wherein the myristoylation is at the N-terminus of the peptide.

21. The method of claim 1, comprising:
administering the agent that inhibits binding of PSD-95 to the NMDAR2B subunit to subjects having a subarachnoid hemorrhage, wherein the damaging effect is reduced in the administered population compared to control subjects not receiving the agent.

22. The method of claim 1, wherein the subject receives endovascular surgery to repair a blood vessel causing the subarachnoid hemorrhage ruptured before the surgery.

23. The method of claim 1, wherein the agent is administered within a period starting 30 minutes before and ending 60 minutes after a surgery.

* * * * *